United States Patent [19]

Kristiansen et al.

[11] Patent Number: 5,468,751
[45] Date of Patent: Nov. 21, 1995

[54] AMINOPYRIMIDINE DERIVATIVES AS MICROBICIDES, INSECTICIDES AND ACARICIDES

[75] Inventors: Odd Kristiansen, Möhlin; Helmut Zondler, Bottmingen; Urs Müller, Müchenstein, all of Switzerland

[73] Assignee: Ciba-Geigy Corporation, Ardsley, N.Y.

[21] Appl. No.: 126,154

[22] Filed: Sep. 23, 1993

Related U.S. Application Data

[63] Continuation of Ser. No. 15,079, Feb. 8, 1993, abandoned, which is a continuation of Ser. No. 910,939, Jul. 19, 1992, abandoned, which is a division of Ser. No. 741,716, Aug. 7, 1991, abandoned.

[30] Foreign Application Priority Data

Aug. 10, 1990 [CH] Switzerland .......................... 2603/90
Feb. 8, 1991 [CH] Switzerland ............................ 390/91

[51] Int. Cl.⁶ .................... A61K 31/505; C07D 239/42; C07D 239/47
[52] U.S. Cl. .......................... 514/256; 514/269; 544/298; 544/319; 544/326; 544/329
[58] Field of Search ...................... 514/256, 269; 544/298, 326, 329, 319

[56] References Cited

U.S. PATENT DOCUMENTS

| | | | |
|---|---|---|---|
| 3,936,454 | 2/1976 | Schwender | 544/322 |
| 4,895,849 | 1/1990 | Yoshioka et al. | 544/229 |
| 4,985,426 | 1/1991 | Yoshioka et al. | 514/241 |
| 5,141,941 | 8/1992 | Fujii et al. | 544/326 |

FOREIGN PATENT DOCUMENTS

| | | |
|---|---|---|
| 057440 | 8/1982 | European Pat. Off. |
| 264217 | 4/1988 | European Pat. Off. |
| 0276406 | 8/1988 | European Pat. Off. |
| 323757 | 7/1989 | European Pat. Off. |
| 326329 | 8/1989 | European Pat. Off. |
| 370704 | 5/1990 | European Pat. Off. |
| 0424125 | 4/1991 | European Pat. Off. |
| 9208704 | 5/1992 | WIPO |

OTHER PUBLICATIONS

Organic Chemistry 2nd Edition, Solomons, 463, 1980.
Chem Abstract vol. 109 (1988) 190439.
Organicum pp. 212, 312–314, 1973.

*Primary Examiner*—Yogendra N. Gupta
*Attorney, Agent, or Firm*—Edward McC. Roberts; Marla J. Mathias

[57] ABSTRACT

Compounds of formula I

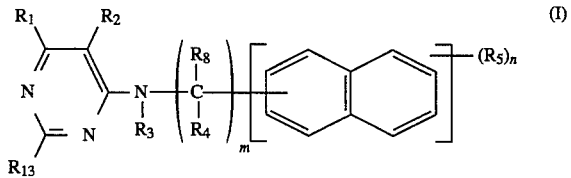

where $R_1$–$R_5$, $R_8$, $R_{13}$, m and n are as defined herein. The novel compounds have valuable biocidal properties. They can be used in crop protection for protecting cultivated plants against attack by pests, and for controlling those pests.

14 Claims, No Drawings

AMINOPYRIMIDINE DERIVATIVES AS MICROBICIDES, INSECTICIDES AND ACARICIDES

This application is a continuation of application Ser. No. 08/015,079, filed Feb. 8, 1993, now abandoned, which is a continuation, of application Ser. No. 07/910,939, filed Jul. 19, 1992, now abandoned, which is a Divisional of Ser. No. 741,716, filed Aug. 7, 1991, now abandoned.

The present invention relates to compounds of formula I, to processes for their preparation and to their use for pest control, and to pesticides that comprise those compounds as active ingredient, together with a suitable carrier.

In the compounds of formula I

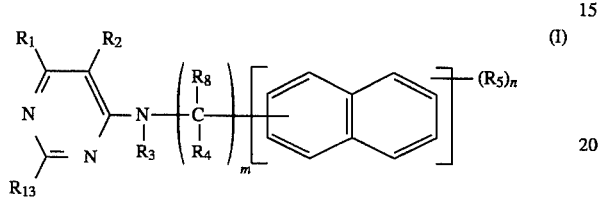

$R_1$ is hydrogen; $C_1$–$C_5$alkyl that is unsubstituted or substituted by halogen or by $C_1$–$C_3$alkoxy or by $S(O)_p$-$C_1$–$C_3$alkyl; $C_2$–$C_7$alkenyl that is unsubstituted or substituted by halogen; $C_3$–$C_7$cycloalkyl; halogen; or $C_2$–$C_4$alkynyl;

$R_2$ is hydrogen; hydroxy; $C_1$–$C_5$alkyl that is unsubstituted or substituted by halogen or by $C_1$–$C_3$alkoxy; $C_1$–$C_4$alkoxy; $S(O)_p$-$C_1$–$C_4$alkyl; halogen; nitro; cyano; amino; $NHR_3$; $N(R_3)R_9$; or $N=C(R_9)R_{10}$;

$R_3$ is hydrogen; $C_1$–$C_5$alkyl; benzyl; —CO—$R_6$; or —S—$R_7$;

$R_4$ and $R_8$ are each independently of the other hydrogen; $C_1$–$C_5$alkyl that is unsubstituted or substituted by halogen or by $C_1$–$C_3$alkoxy; or $C_3$–$C_7$cycloalkyl;

$R_5$ is halogen; $C_1$–$C_3$alkyl; $C_1$–$C_3$alkoxy; $C_2$–$C_6$alkoxyalkyl; $C_1$–$C_3$haloalkyl; $C_1$–$C_3$alkylthio; $C_1$–$C_3$haloalkoxy; $C_1$–$C_3$haloalkylthio; CN; $NO_2$; or an —X-phenyl group that occurs once at the naphthyl ring and that is unsubstituted or mono- to tri-substituted by identical or different substituents selected from halogen, $C_1$–$C_3$alkyl and $C_1$–$C_3$alkoxy;

$R_6$ is $C_1$–$C_5$alkyl; or phenyl that is unsubstituted or substituted by halogen and/or by $C_1$–$C_3$alkyl;

$R_7$ is phenyl or benzyl each of which is unsubstituted or mono- or di-substituted in the ring by identical or different substituents selected from halogen, nitro and cyano; or $C_1$–$C_5$alkyl that is unsubstituted or substituted by halogen or by cyano;

$R_9$ is $C_1$–$C_5$alkyl;

$R_{10}$ is hydrogen or $C_1$–$C_5$alkyl;

$R_{13}$ is hydrogen; $C_1$–$C_4$alkyl that is unsubstituted or substituted by halogen or by $C_1$–$C_3$alkoxy; cyclopropyl; halogen; $C_1$–$C_3$alkoxy; $C_1$–$C_3$alkylthio; or —N($C_1$–$C_3$alkyl)$_2$;

X is oxygen or sulfur, m is 1, 2 or 3;

n is 0, 1, 2 or 3; and p is 0, 1 or 2.

Preference is given to compounds of formula I wherein:

1.1

$R_1$ is hydrogen; $C_1$–$C_5$alkyl; $C_1$–$C_5$alkyl substituted by $S(O)_p$-$C_1$–$C_3$alkyl; $C_1$–$C_5$haloalkyl having from 1 to 5 halogen atoms; $_2$–$C_6$alkoxyalkyl; $C_2$–$C_7$alkenyl; $C_2$–$C_7$haloalkenyl having 1 or 2 halogen atoms; $C_3$–$C_6$cycloalkyl; halogen; or $C_2$–$C_4$alkynyl;

$R_2$ is hydrogen; $C_1$–$C_5$alkyl; $C_1$–$C_5$haloalkyl having from 1 to 5 halogen atoms; $C_2$–$C_6$alkoxyalkyl; nitro; cyano; $S(O)_p$-$C_1$–$C_3$alkyl; amino; $NHR_3$; $N(R_3)R_9$; $N=C(R_9)R_{10}$; or halogen;

$R_3$ is hydrogen; $C_1$–$C_5$alkyl; benzyl; —CO—$R_6$; or —S—$R_7$;

$R_4$ and $R_8$ are each independently of the other hydrogen; $C_1$–$C_5$alkyl; $C_1$–$C_5$haloalkyl having from 1 to 3 halogen atoms; $C_2$–$C_6$alkoxyalkyl; or $C_3$–$C_6$cycloalkyl;

$R_5$ is halogen; $C_1$–$C_3$alkyl; $C_1$–$C_3$alkoxy; $C_1$–$C_6$alkoxyalkyl; $C_1$–$C_3$haloalkyl; $C_1$–$C_3$alkylthio; $C_1$–$C_3$haloalkoxy; $C_1$–$C_3$haloalkylthio; CN; $NO_2$; or an X-phenyl group that occurs at the naphthyl ring and that is unsubstituted or mono- to tri-substituted by identical or different substituents selected from halogen, $C_1$–$C_3$alkyl and $C_1$–$C_3$alkoxy;

$R_6$ is $C_1$–$C_5$alkyl; or phenyl that is unsubstituted or substituted by halogen and/or by $C_1$–$C_3$alkyl;

$R_7$ is phenyl or benzyl each of which is unsubstituted or mono- or di-substituted in the ring by identical or different substituents selected from halogen, nitro and cyano; or $C_1$–$C_5$alkyl that is unsubstituted or substituted by halogen or by cyano;

X is oxygen or sulfur;

$R_9$ is $C_1$–$C_5$alkyl;

$R_{10}$ is hydrogen or $C_1$–$C_5$alkyl;

m is 1, 2 or 3;

n is 0, 1, 2 or 3; and p is 0, 1 or 2.

1.2

$R_1$ is hydrogen; $C_1$–$C_5$alkyl substituted by $S(O)_p$-$C_1$–$C_3$alkyl; $C_1$–$C_5$alkyl; $C_1$–$C_3$haloalkyl having from 1 to 3 halogen atoms; $C_2$–$C_5$alkoxyalkyl; $C_2$–$C_5$alkenyl; $C_2$–$C_5$haloalkenyl having 1 to 3 halogen atoms; $C_3$–$C_5$cycloalkyl; halogen; or $C_2$–$C_4$alkynyl;

$R_2$ is hydrogen; $C_1$–$C_5$alkyl; $C_1$–$C_3$haloalkyl having from 1 to 3 halogen atoms; $C_2$–$C_5$alkoxyalkyl; nitro; cyano; $S(O)_p$-$C_1$–$C_3$alkyl; amino; $NHR_3$; $N(R_3)R_9$; $N=C(R_9)R_{10}$; or halogen;

$R_3$ is hydrogen; $C_1$–$C_5$alkyl; benzyl; —CO—$R_6$; or —S—$R_7$;

$R_4$ and $R_8$ are each independently of the other hydrogen; $C_1$–$C_5$alkyl; $C_1$–$C_5$haloalkyl having from 1 to 3 halogen atoms; $C_2$–$C_5$alkoxyalkyl; or $C_3$–$C_6$cycloalkyl;

$R_5$ is halogen; $C_1$–$C_3$alkyl; $C_1$–$C_3$alkoxy; $C_1$–$C_6$allkoxyalkyl; $C_1$–$C_3$ haloalkyl; $C_1$–$C_3$alkylthio; $C_1$–$C_3$haloalkoxy; $C_1$–$C_3$haloalkylthio; CN; $NO_2$; or an X-phenyl group that occurs at the naphthyl ring and that is unsubstituted or mono- to tri-substituted by identical or different substituents selected from halogen, $C_1$–$C_3$alkyl and $C_1$–$C_3$alkoxy;

$R_6$ is $C_1$–$C_5$alkyl; or phenyl that is unsubstituted or substituted by halogen and/or by $C_1$–$C_3$alkyl;

$R_7$ is phenyl or benzyl each of which is unsubstituted or mono- or di-substituted in the ring by identical or different substituents selected from halogen, nitro and cyano; or $C_1$–$C_5$alkyl that is unsubstituted or substituted by halogen or by cyano;

X is oxygen or sulfur;

$R_9$ is $C_1$–$C_5$alkyl;
$R_{10}$ is hydrogen or $C_1$–$C_5$alkyl;
m is 1, 2 or 3;
n is 0, 1, 2 or 3; and
p is 0, 1 or 2.

1.3 Also compounds of formula I'

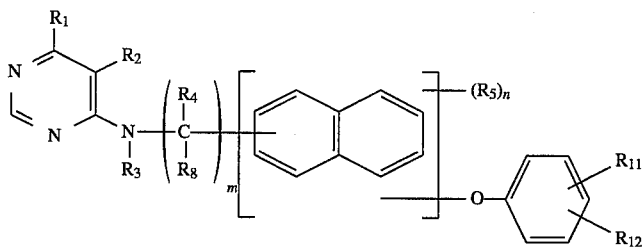

(I')

wherein:
$R_1$ is hydrogen; $C_1$–$C_5$alkyl; $C_1$–$C_5$alkyl substituted by S(O)$_p$-$C_1$–$C_5$alkyl; $C_1$–$C_3$haloalkyl having from 1 to 3 halogen atoms; $C_2$–$C_5$alkoxyalkyl; $C_2$–$C_5$alkenyl; $C_2$–$C_5$haloalkenyl having from 1 to 3 halogen atoms; $C_3$–$C_6$cycloalkyl; halogen; or $C_2$–$C_4$alkynyl;
$R_2$ is hydrogen; $C_1$–$C_5$alkyl; $C_1$–$C_3$haloalkyl having from 1 to 3 halogen atoms; $C_3$–$C_5$alkoxyalkyl; nitro; cyano; S(O)$_p$-$C_1$–$C_3$alkyl; amino; NHR$_3$; N(R$_3$)R$_9$; N=C(R$_9$)R$_{10}$; or halogen;
$R_3$ is hydrogen; $C_1$–$C_5$alkyl; benzyl; —CO—R$_6$; or —S—R$_7$;
$R_4$ and $R_8$ are each independently of the other hydrogen; $C_1$–$C_5$alkyl; $C_1$–$C_5$haloalkyl having from 1 to 3 halogen atoms; $C_2$–$C_6$alkoxyalkyl; or $C_3$–$C_6$cycloalkyl;
$R_5$ is halogen; $C_1$–$C_3$alkyl; $C_1$–$C_3$alkoxy; CrC$_3$haloalkyl; or $C_1$–$C_3$haloalkoxy;
$R_6$ is $C_1$–$C_5$alkyl; or phenyl that is unsubstituted or substituted by halogen and/or by $C_1$–$C_3$alkyl;
$R_7$ is phenyl or benzyl each of which is unsubstituted or mono- or di-substituted in the ring by identical or different substituents selected from halogen, nitro and cyano; or $C_1$–$C_5$alkyl that is unsubstituted or substituted by halogen or by cyano;
$R_9$ is $C_1$–$C_5$alkyl;
$R_{10}$ is hydrogen or $C_1$–$C_5$alkyl;
$R_{11}$ and $R_{12}$ are each independently of the other halogen, $C_1$–$C_3$alkyl or $C_1$–$C_3$alkoxy;
m is 1, 2 or 3;
n is 0, 1 or 2; and
p is 0, 1 or 2.

1.4 Also compounds of formula I' wherein
$R_1$ to $R_4$ and $R_8$ are as defined under formula I;
$R_5$ is halogen, $C_1$–$C_3$alkyl, CF$_3$, $C_2$–$C_5$alkoxyalkyl or $C_1$–$C_3$alkoxy;
$R_{11}$ and $R_{12}$ are each independently of the other hydrogen, halogen or $C_1$–$C_3$alkyl;
m is 1, 2 or 3; and
n is 0, 1 or 2.

1.5 Compounds of formula I wherein:
$R_1$ is hydrogen; $C_1$–$C_5$alkyl; $C_1$–$C_5$haloalkyl having from 1 to 3 halogen atoms; $C_2$–$C_5$alkoxyalkyl; $C_2$–$C_5$alkenyl; $C_2$–$C_5$haloalkenyl; or halogen;
$R_2$ is hydrogen; $C_1$–$C_5$alkyl; $C_1$–$C_3$haloalkyl having from 1 to 3 halogen atoms; $C_3$–$C_5$alkoxyalkyl; nitro; cyano; S(O)$_p$-$C_1$–$C_4$alkyl; amino; NHR$_3$; N(R$_3$)R$_9$; N=C(R$_9$)R$_{10}$; or halogen;

$R_3$ is hydrogen; $C_1$–$C_3$alkyl; benzyl; —CO—R$_6$; or SR$_7$;
$R_4$ and $R_8$ are each independently of the other hydrogen; $C_1$–$C_5$alkyl; $C_1$–$C_5$haloalkyl having from 1 to 3 halogen atoms; $C_2$–$C_6$alkoxyalkyl; or $C_3$–$C_6$cycloalkyl;

$R_5$ is halogen; $C_1$–$C_3$alkyl; $C_1$–$C_3$alkoxy; $C_1$–$C_6$allkoxyalkyl; $C_1$–$C_3$haloalkyl; $C_1$–$C_3$alkylthio; $C_1$–$C_3$haloalkoxy; $C_1$–$C_3$haloalkylthio; cyano; or nitro;
$R_6$ is $C_1$–$C_5$alkyl; phenyl; or phenyl substituted by halogen and/or by $C_1$–$C_3$alkyl;
$R_7$ is phenyl; phenyl mono- or di-substituted by halogen, nitro or by cyano; benzyl; benzyl mono- or di-substituted in the ring by halogen, nitro or by cyano; $C_1$–$C_5$alkyl; or $C_1$–$C_5$alkyl substituted by halogen or by cyano;
$R_9$ is $C_1$–$C_5$alkyl;
$R_{10}$ is hydrogen or $C_1$–$C_3$alkyl;
$R_{13}$ is hydrogen or $C_1$–$C_4$alkyl;
m is 1, 2 or 3;
n is 0, 1 or 2; and
p is 0, 1 or 2.

1.6 Compounds of group 1.5 wherein:
$R_1$ is $C_1$–$C_5$alkyl; CF$_3$; $C_2$–$C_5$alkoxyalkyl; $C_2$–$C_4$alkenyl; $C_2$–$C_4$monohaloalkenyl; or halogen;
$R_2$ is $C_1$–$C_5$alkyl or halogen;
$R_3$ is hydrogen or $C_1$–$C_3$alkyl;
$R_4$ is hydrogen; $C_1$–$C_3$alkyl; or cyclopropyl;
$R_5$ is halogen; $C_1$–$C_2$alkyl; or $C_1$–$C_3$alkoxy;
$R_8$ is hydrogen;
n is 0, 1 or 2; and
m is 1.

1.7 Compounds of group 1.6 wherein:
$R_1$ is $C_1$–$C_4$alkyl; CF$_3$; $C_2$–$C_4$alkoxyalkyl; $C_2$–$C_4$alkenyl; or halogen;
$R_2$ is $C_1$–$C_4$alkyl or halogen;
$R_3$ is hydrogen or $C_1$–$C_3$alkyl;
$R_4$ is hydrogen or $C_1$–$C_3$alkyl;
$R_5$ is halogen; methyl; ethyl; or methoxy;
$R_8$ is hydrogen;
n is 0, 1, 2 or 3; and
m is 1.

1.8 Compounds of group 1.7 of formula I''

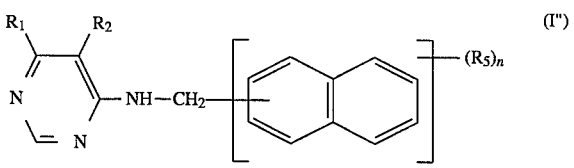

(I'')

wherein:
$R_1$ is $C_1$–$C_4$alkyl, CF$_3$, $C_2$–$C_4$alkoxyalkyl or halogen;

$R_2$ is $C_1$–$C_4$alkyl or halogen;
$R_5$ is chlorine, bromine, methyl, ethyl or methoxy; and
n is 0, 1 or 2.

1.9 Compounds of formula I'''

$$\underset{N}{\overset{R_1}{\underset{\|}{\diagdown}}}\overset{R_2}{\underset{\diagup}{=}}\overset{}{\underset{N}{\diagdown}}\overset{R_8}{\underset{R_3}{\overset{|}{N-\left(\overset{|}{\underset{|}{C}}\right)_m}}}\text{—[naphthyl]—}R_5 \qquad (\text{I'''})$$

wherein:
$R_1$ is hydrogen, $C_1$–$C_3$alkyl, $CF_3$ or halogen;
$R_2$ is hydrogen, $C_1$–$C_3$alkyl, halogen, $NO_2$ or $S(O)_p$-$C_1$–$C_3$alkyl;
$R_3$ is hydrogen;
$R_4$ is methyl, ethyl, isopropyl, n-propyl or cyclopropyl;
$R_8$ is hydrogen, methyl or ethyl;
$R_5$ is hydrogen, halogen, $C_1$–$C_3$alkyl, $OCHF_2$, $CF_3$, $NO_2$ or $C_1$–$C_3$alkoxy;
m is 1 or 2; and
p is 0, 1 or 2.

1.10 Compounds of group 1.2 wherein:
$R_1$ is hydrogen; $C_1$–$C_5$alkyl; $C_1$–$C_3$haloalkyl having from 1 to 3 halogen atoms; $C_2$–$C_5$alkoxyalkyl; $C_2$–$C_5$alkenyl; $C_2$–$C_5$haloalkenyl having from 1 to 3 halogen atoms; $C_3$–$C_6$cycloalkyl; or halogen;
$R_2$ is hydrogen; $C_1$–$C_5$alkyl; $C_1$–$C_3$haloalkyl having from 1 to 3 halogen atoms; $C_3$–$C_5$alkoxyalkyl; nitro; cyano; $S(O)_p$-$C_1$–$C_4$alkyl; amino; $NHR_3$; $N(R_3)R_9$; $N=C(R_9)R_{10}$; or halogen;
$R_3$ is hydrogen; $C_1$–$C_5$alkyl; benzyl; $COR_6$; or $SR_7$;
$R_4$ and $R_8$ are each independently of the other hydrogen; $C_1$–$C_5$alkyl; $C_1$–$C_5$haloalkyl having from 1 to 3 halogen atoms; $C_2$–$C_6$alkoxyalkyl; or $C_3$–$C_6$cycloalkyl;
$R_5$ is halogen; $C_1$–$C_3$alkyl; $C_1$–$C_3$alkoxy; $C_1$–$C_6$alkoxyalkyl; $C_1$–$C_3$haloalkyl; $C_1$–$C_3$alkylthio; $C_1$–$C_3$haloalkoxy; $C_1$–$C_3$haloalkylthio; cyano; nitro; or an X-phenyl group that occurs at the naphthyl ring and that is unsubstituted or mono- to tri-substituted by identical or different substituents selected from halogen, $C_1$–$C_3$alkyl and $C_1$–$C_3$alkoxy;
$R_6$ is $C_1$–$C_5$alkyl; phenyl; or phenyl substituted by halogen and/or by $C_1$–$C_3$alkyl;
$R_7$ is phenyl; phenyl mono- or di-substituted by identical or different substituents selected from halogen, nitro and cyano; benzyl; benzyl mono- or di-substituted in the ring by identical or different substituents selected from halogen, nitro and cyano; $C_1$–$C_5$alkyl; or $C_1$–$C_5$alkyl substituted by halogen or by cyano;
$R_9$ is $C_1$–$C_5$alkyl;
$R_{10}$ is hydrogen or $C_1$–$C_5$alkyl;
$R_{13}$ is hydrogen;
X is oxygen or sulfur;
m is 2 or 3;
n is 0, 1, 2 or 3; and
p is 0, 1 or 2.

1.11 Compounds of group 1.10 wherein:
$R_1$ is hydrogen; $C_1$–$C_3$alkyl; $C_1$–$C_3$haloalkyl having from 1 to 3 halogen atoms; $C_2$–$C_5$alkoxyalkyl; $C_2$–$C_5$alkenyl; $C_3$–$C_6$cycloalkyl; or halogen;
$R_2$ is hydrogen; $C_1$–$C_5$alkyl; $C_1$–$C_3$haloalkyl having from 1 to 3 halogen atoms; $C_3$–$C_5$alkoxyalkyl; nitro; cyano; $S(O)_p$-$C_1$–$C_3$alkyl; amino; $NHR_3$; $N(R_3)R_9$; $N=C(R_9)R_{10}$; or halogen;
$R_3$ is hydrogen or $C_1$–$C_3$alkyl;
$R_4$ and $R_8$ are each independently of the other hydrogen; $C_1$–$C_5$alkyl; $CF_3$; $C_2$–$C_6$alkoxyalkyl; or $C_3$–$C_6$cycloalkyl;
$R_5$ is halogen; $C_1$–$C_3$alkyl; $C_1$–$C_3$alkoxy; $C_2$–$C_6$alkoxyalkyl; $C_1$–$C_3$haloalkyl; $C_1$–$C_3$alkylthio; $C_1$–$C_3$haloalkoxy; $C_1$–$C_3$haloalkylthio; cyano; or nitro;
$R_6$ is $C_1$–$C_5$alkyl; phenyl; or phenyl substituted by halogen and/or by $C_1$–$C_3$alkyl;
$R_7$ is phenyl; phenyl mono- or di-substituted by identical or different substituents selected from halogen, nitro and cyano; benzyl; benzyl mono- or di-substituted in the ring by identical or different substituents selected from halogen, nitro and cyano; $C_1$–$C_5$alkyl; or $C_1$–$C_5$alkyl substituted by halogen or by cyano;
$R_9$ is $C_1$–$C_5$alkyl;
$R_{10}$ is hydrogen or $C_1$–$C_5$alkyl;
$R_{13}$ is hydrogen;
X is oxygen or sulfur;
m is 2 or 3;
n is 0, 1, 2 or 3; and
p is 0, 1 or 2.

1.12 Compounds of group 1.11 wherein:
$R_1$ is hydrogen; $C_1$–$C_3$alkyl; $CF_3$; $C_2$–$C_5$alkoxyalkyl; $C_2$–$C_5$alkenyl; $C_3$–$C_6$cycloalkyl; or halogen;
$R_2$ is hydrogen; $C_1$–$C_5$alkyl; $CF_3$; $C_3$–$C_5$alkoxyalkyl; nitro; cyano; $S(O)_p$-$C_1$–$C_4$alkyl; amino; $N(R_3)R_9$; $N=C(R_9)R_{10}$; or halogen;
$R_3$ is hydrogen;
$R_4$ and $R_8$ are each independently of the other hydrogen; $C_1$–$C_5$alkyl; $C_2$–$C_6$alkoxyalkyl; or $C_3$–$C_6$cycloalkyl;
$R_5$ is halogen; $C_1$–$C_3$alkyl; $C_1$–$C_3$alkoxy; $C_2$–$C_6$alkoxyalkyl; haloalkyl; $C_1$–$C_3$alkylthio; $C_1$–$C_3$haloalkoxy; $C_1$–$C_3$haloalkylthio; nitro; or cyano;
$R_6$ is $C_1$–$C_5$alkyl; phenyl; or phenyl substituted by halogen and/or by $C_1$–$C_3$alkyl;
$R_7$ is phenyl; phenyl mono- or di-substituted by identical or different substituents selected from halogen, nitro and cyano; benzyl; benzyl mono- or di-substituted in the ring by identical or different substituents selected from halogen, nitro and cyano; $C_1$–$C_5$alkyl; or $C_1$–$C_5$alkyl substituted by halogen or by cyano;
$R_9$ is $C_1$–$C_5$alkyl;
$R_{10}$ is hydrogen or $C_1$–$C_5$alkyl;
$R_{13}$ is hydrogen;
X is oxygen or sulfur;,
m is 2;
n is 0, 1, 2 or 3; and
p is 0, 1 or 2.

1.13 Compounds of group 1.12 wherein:
$R_1$ is hydrogen; $C_1$–$C_3$alkyl; $CF_3$; $C_2$–$C_5$alkoxyalkyl; $C_2$–$C_5$alkenyl; $C_3$–$C_6$cycloalkyl; or halogen;
$R_2$ is hydrogen; $C_1$–$C_5$alkyl; $CF_3$; $C_3$–$C_5$alkoxyalkyl; nitro; cyano; $S(O)_p$-$C_1$–$C_3$alkyl; amino; $N(R_3)R_9$; $N=C(R_9)R_{10}$; or halogen;
$R_3$ is hydrogen;
$R_4$ and $R_8$ are each independently of the other hydrogen; $C_1$–$C_5$alkyl; $C_2$–$C_6$alkoxyalkyl; or $C_3$–$C_6$cycloalkyl;
$R_5$ is halogen; $C_1$–$C_3$alkyl; $C_1$–$C_3$alkoxy; $C_2$–$C_6$alkoxyalkyl; $C_1$–$C_3$haloalkyl; $C_1$–$C_3$alkylthio; $C_1$–$C_3$haloalkoxy;

$C_1$–$C_3$haloalkylthio; nitro; or cyano;

$R_6$ is $C_1$–$C_5$alkyl; phenyl; or phenyl substituted by halogen and/or by $C_1$–$C_3$alkyl;

$R_7$ is phenyl; phenyl mono- or di-substituted by identical or different substituents selected from halogen, nitro and cyano; benzyl; benzyl mono- or di-substituted in the ring by identical or different substituents selected from halogen, nitro and cyano; $C_1$–$C_5$alkyl; or $C_1$–$C_5$alkyl substituted by halogen or by cyano;

$R_9$ is $C_1$–$C_3$alkyl;

$R_{10}$ is hydrogen or $C_1$–$C_3$alkyl;

$R_{13}$ is hydrogen;

X is oxygen or sulfur;

m is 3;

n is 0, 1, 2 or 3; and p is 0, 1 or 2.

A special group of compounds of the present invention comprises the compounds of formula Ia:

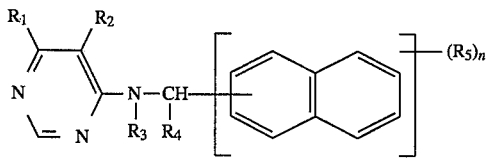

wherein:

$R_1$ is $C_1$–$C_5$alkyl that is unsubstituted or substituted by halogen or by $C_1$–$C_3$ alkoxy; $C_2$–$C_7$alkenyl that is unsubstituted or substituted by halogen; $C_3$–$C_7$cycloalkyl; or halogen;

$R_2$ is $C_1$–$C_5$alkyl that is unsubstituted or substituted by halogen or by $C_1$–$C_3$alkoxy; halogen; nitro; or cyano;

$R_3$ is hydrogen; $C_1$–$C_5$alkyl; benzyl; —CO—$R_6$ or —S—$R_7$;

$R_4$ is hydrogen; $C_1$–$C_5$alkyl that is unsubstituted or substituted by halogen or by $C_1$–$C_3$alkoxy; or $C_3$–$C_7$cycloalkyl;

$R_5$ is halogen; $C_1$–$C_3$alkyl; $C_1$–$C_3$alkoxy; $C_1$–$C_3$alkylthio; or an —X-phenyl group that occurs once at the phenyl ring and that is unsubstituted or mono- to tri-substituted by identical or different substituents selected from halogen, $C_1$–$C_3$alkyl and $C_1$–$C_3$alkoxy;

$R_6$ is $C_1$–$C_5$alkyl; or phenyl that is unsubstituted or substituted by halogen and/or by $C_1$–$C_3$alkyl;

$R_7$ is phenyl or benzyl each of which is unsubstituted or mono- or di-substituted in the ring by identical or different substituents selected from halogen, nitro and cyano; or $C_1$–$C_5$alkyl that is unsubstituted or substituted by halogen or by cyano;

X is oxygen or sulfur; and n is 0, 1, 2 or 3.

In view of their biological activity in the control of pests, the following compounds are to be regarded as preferred:

(d,l)-4-[1'-(β-naphthyl)-ethylamino]-5-chloro-6-ethylpyrimidine (comp. 1.2);

(−)-4-[1'-(β-naphthyl)-ethylamino]-5-chloro-6-ethylpyrimidine (comp. 1.73);

(d,l)-4-[1'-(β-naphthyl)-propylamino]-5-chloro-6-ethylpyrimidine (comp. 1.3);

(d,l)-4-[1'-(β-naphthyl)-ethylamino]-5-chloro-6-methylpyrimidine (comp. 1.53);

(d,l)-4-[1'-(2-(6-bromonaphthyl))-ethylamino]-5-chloro-6-ethylpyrimidine (comp. 1.149);

(d,l)-4-[1'-(β-naphthyl)-ethylamino]-5-bromo-6-ethylpyrimidine (comp. 1.84);

(d,l)-4-[1'-(β-naphthyl)-ethylamino]-5-chloro-6-n-propylpyrimidine (comp. 1.86);

(d,l)-4-[1'-(β-naphthyl)-ethylamino]-5-iodo-6-ethylpyrimidine (comp. 1.100).

Depending upon the number of carbon atoms indicated, alkyl by itself or as a constituent of another substituent, such as haloalkyl, alkoxy or alkylthio, is to be understood as being, for example, methyl, ethyl, propyl, butyl, pentyl and their isomers, for example isopropyl, isobutyl, isoamyl, tert-butyl or sec-butyl.

$C_2$–$C_7$alkenyl is an aliphatic radical having a double bond, for example allyl, vinyl, methallyl, crotyl, butenyl, pentenyl, etc.

Halogen is fluorine, chlorine, bromine or iodine.

Haloalkyl denotes mono- to per-halogenated radicals, for example $CHCl_2$, $CH_2F$, $CCl_3$, $CH_2Cl$, $CHF_2$, $CF_3$, $CH_2CH_2Br$, $C_2Cl_5$, $CH_2Br$, $CHBrCl$, etc., preferably $CF_3$ and $CHF_2$.

Depending upon the number of carbon atoms indicated, cycloalkyl is, for example, cyclopropyl, cyclobutyl, cyclopentyl, cyclohexyl or cycloheptyl.

4-Aminopyrimidine compounds are already known, for example from EP-A-264 217. The compounds of formula I according to the invention differ characteristically from the known compounds by the combination of a 4-aminopyrimidine ring with a naphthylalkyl radical, as a result of which an unexpectedly high microbicidal and insecticidal/acaricidal activity is achieved in the novel compounds.

The compounds of formula I are oils, resins or solids that are stable at room temperature. They can be used preventively and curatively in the agricultural sector or related fields for controlling plant-destructive microorganisms, insects, and pests of the order Acarina. The compounds of formula I according to the invention are, when used in low concentrations, distinguished not only by excellent activity, but also by the fact that they are especially well tolerated by plants.

The compounds of formula I can have an asymmetric carbon atom in the position adjacent to $R_4$ and can therefore be in enantiomeric and diastereoisomeric forms. In general, the preparation of these compounds results in a mixture of enantiomers or diastereoisomers. These mixtures can be cleaved into the pure optical antipodes in customary manner, for example by fractional crystallisation of salts with optically active acids. However, such compounds can also be prepared selectively by diastereo- or enantio-selective methods. The enantiomers can have different biological activities.

The present invention therefore relates to the racemic compounds and all isomers of formula I, to their preparation and to their use in crop protection, and to compositions that comprise those compounds as active ingredients.

Compounds of formula I can be obtained by various preparation variants, for example by reacting a compound of formula II

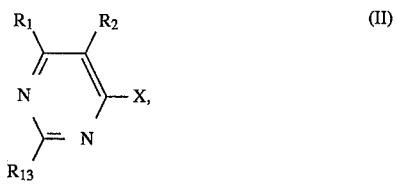

wherein $R_1$, $R_2$ and $R_{13}$ are as defined for formula I and X is a readily removable radical, with a compound of formula III

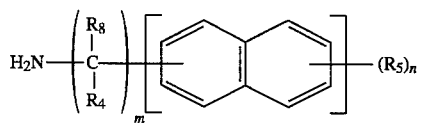

wherein $R_4$, $R_5$, $R_8$, m and n are as defined for formula I, preferably in the presence of a base. The substituent $R_3$ (alkyl, benzyl, acyl or —S—$R_7$) can then be introduced by corresponding N-alkylation, N-benzylation, N-acylation, N-thioalkylation or N-thioarylation, respectively.

Examples of readily removable radicals are halogen, such as chlorine, bromine or iodine; $C_1$–$C_6$alkylthio radicals, such as methylthio, ethylthio or propylthio; (halo)alkanesulfonyloxy groups, such as mesyloxy, ethanesulfonyloxy or trifluoromethanesulfonyloxy; and arylsulfonyloxy groups, such as benzenesulfonyloxy or tosyloxy.

Suitable bases for facilitating the removal of HX are inorganic bases, such as potassium or sodium carbonate, NaH, etc. Also suitable are organic bases, such as triethylamine, pyridine, N,N-diethylaniline, triethylenediamine, etc. 4-(N,N-dimethylamino)pyridine is preferred on account of its catalytic activity.

The reactants can react with one another as such without the addition of a solvent, for example in the molten state. In the majority of cases, however, it is advantageous to add a solvent or several solvents or diluents. There may be mentioned as examples aromatic, aliphatic and alicyclic hydrocarbons and halogenated hydrocarbons, for example benzene, toluene, xylene, chlorobenzene, bromobenzene, petroleum ether, hexane, cyclohexane, methylene chloride, chloroform, dichloroethane, trichloroethylene; ethers, such as diethyl ether, tetrahydrofuran THF), dioxane, tert-butyl methyl ether; ketones, such as acetone, methyl ethyl ketone; alcohols, such as methanol, ethanol, propanol, butanol, ethylene glycol, glycerol; amides, such as dimethylformamide (DMF), N,N-dimethylacetamide; also acetonitrile, dimethyl sulfoxide (DMSO), and also a base added in excess, such as pyridine, N,N-diethylaniline, triethylamine, etc.

The subsequent N-alkylation or N-benzylation to introduce the substituent $R_3$ is effected in customary manner with an alkyl or benzyl halide, especially the corresponding bromide, in the presence of a strong base. An N-acylation is carried out in customary manner with a $C_1$–$C_6$alkanecarboxylic acid or with a benzoic acid or an acid halide thereof, especially an acid chloride or bromide, in inert dry solvents. An N-thioalkylation or N-thioarylation is advantageously carried out with the corresponding sulfenyl chloride in the presence of a base.

According to another process variant, where the substituent $R_3$ is to be $C_1$–$C_5$alkyl, benzyl or —S—$R_7$, the compound of formula II can also be reacted directly with a compound of formula IV:

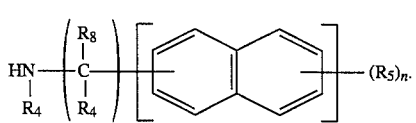

In this case, the presence of strong bases is essential.

The temperature in the above-mentioned processes is from 0° to 180° C., preferably from 20° to 130° C., and in many cases corresponds to the reflux temperature of the solvent.

The following pyrimidine compounds of formula II' are novel:

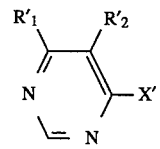

wherein $R'_1$ is $CH_3$, $C_2H_5$, n-$C_3H_7$, n-$C_4H_9$, $CH(CH_3)_2$ or $CF_3$;

$R'_2$ is hydrogen, fluorine, chlorine, bromine, iodine, nitro or amino; and

X' is hydroxy or chlorine;

with the proviso that the following conditions may not apply simultaneously:

1) $R'_1$ is $CH_3$ or $C_2H_5$; $R'_2$ is hydrogen or chlorine; and X' is hydroxy or chlorine;

2) $R'_1$ is $CH_3$; $R'_2$ is bromine, iodine, nitro or amino; and X' is hydroxy or chlorine;

3) $R'_1$ is n-$C_3H_7$ or $CH(CH_3)$; $R'_2$ is hydrogen; and X' is hydroxy;

4) $R'_1$ is $CF_3$; $R'_2$ is hydrogen; and X' is hydroxy or chlorine;

5) $R'_1$ is $CF_3$; $R'_2$ is chlorine, bromine or iodine; and X' is hydroxy;

6) $R'_1$ is $CH_3$ or n-$C_4H_9$; $R'_2$ is fluorine; and X' is hydroxy.

The present invention relates to the novel compounds of formula II'.

Pyrimidines of formula II are either already known or are prepared according to general methods of synthesis (see D. J. Brown "The Pyrimidines" in Heterocyclic Compounds).

According to D. J. Brown (ibid., page 10), the nitration of pyrimidines requires at least two electron donors as substituents, and for that reason nitration of 6-alkyl-4-hydroxypyrimidines does not occur under the customary nitration conditions even in mixtures of 100% nitric acid and 100% sulfuric acid. Surprisingly, however, the 6-alkyl-4-hydroxy-5-nitropyrimidines can be prepared in oleum instead of in 100% sulfuric acid:

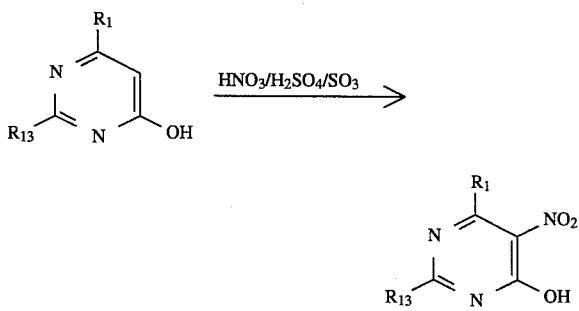

In this reaction, it is necessary to keep the temperatures as low as possible in order to suppress secondary reactions. Temperatures of from 10° to 70° C., preferably from 20° to 40° C., have proved advantageous. There comes into consideration as the oleum $H_2SO_4$ containing from 5 to 70% $SO_3$, especially from 10 to 40% $SO_3$.

The above-described nitration of pyrimidine compounds is a novel preparation process, and the present invention relates especially to that process.

Chlorine, bromine and iodine can readily be introduced into the 5-position of the 4-hydroxypyrimidines analogously to the methods described in the literature:

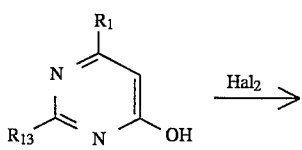

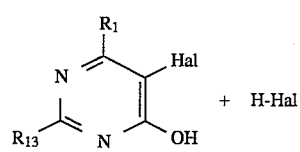

In this reaction, the halogens are metered into an aqueous solution or suspension of the pyrimidines, and the resulting acid is neutralised. Aliphatic carboxylic acids, for example acetic acid, are also suitable solvents for the halogenation reactions.

The 4-hydroxypyrimidines are converted into the 4-chloropyrimidines in accordance with generally customary methods, preferably using phosphorus oxychloride:

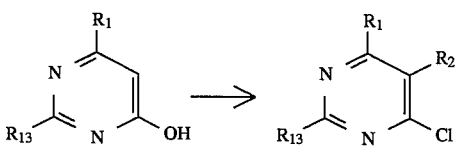

It is possible to carry out this reaction with an excess of phosphorus oxychloride without a solvent, or inert solvents, for example toluene or xylene, are used. In many cases, the addition of organic bases, for example dimethyl- or diethylaniline, has an advantageous effect on the yield. The reaction is carried out in a temperature range of from 20° to 140° C., preferably from 40° to 100° C.

Reduction of the 5-nitropyrimidines yields the 5-aminopyrimidines:

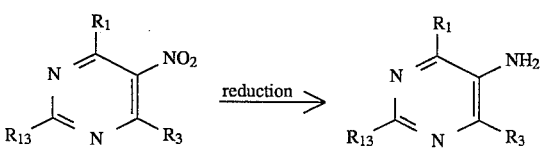

The generally customary reducing agents can be used for this purpose, for example iron or zinc powder in solvents, for example acetic acid, or hydrogen activated by a metal catalyst.

Some pyrimidines of formula II can be prepared in accordance with the following reaction scheme.

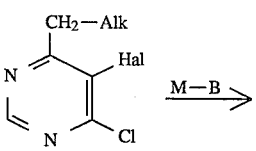

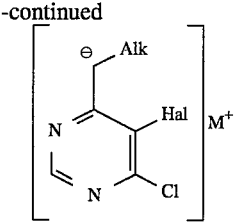

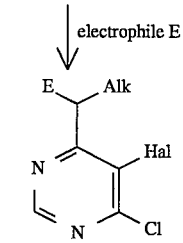

The bases (M-B) used are organo-alkali metal/alkaline-earth metal compounds, for example alkyllithium, or, preferably, lithium dialkylamino compounds, for example lithium diisopropylamine. The electrophiles used may be, for example, haloalkyl compounds, such as alkyl iodides, allyl bromides or alkyl-$SO_2$—S-alkyl, and other generally customary electrophiles.

The radicals $R_1$ and $R_2$ mentioned in the above-described preparation processes are as defined under formula I, and Hal is halogen.

Compounds of formula (I) wherein $R_2$ is halogen or $NO_2$ can also be prepared by halogenating or nitrating compounds (I) ($R_2$=H) that are unsubstituted in the 5-position.

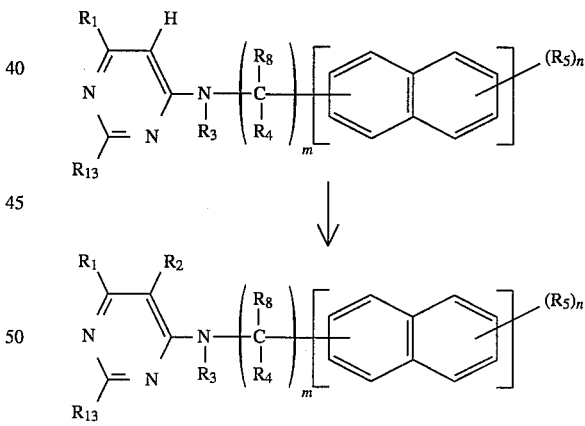

The halogenation or nitration reactions are carried out under the conditions mentioned above for the preparation of the 4-hydroxypyrimidines.

Naphthalene derivatives of formulae III and IV are also known from the literature, or they can be prepared by known methods, for example as follows:

1) from the corresponding aldehydes or ketones by reaction with amines and formic acid or formamide and formic acid according to LEUCKART and WALLACH

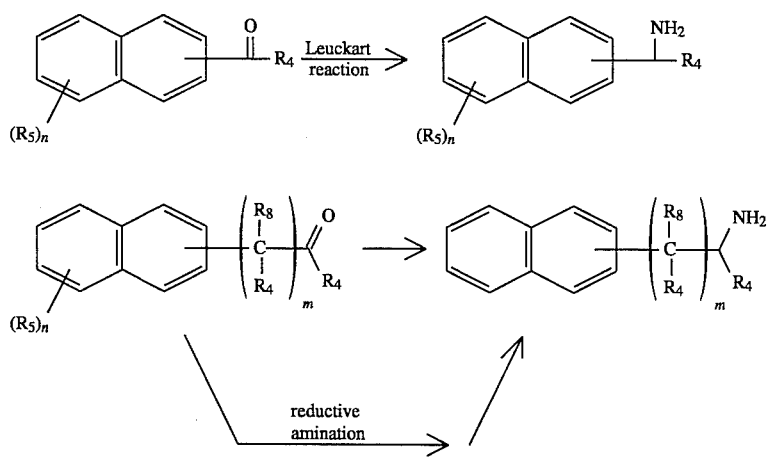

or by reductive amination of the aldehydes or ketones with $NH_2$—$R_3$ and hydrogen in the presence of metal catalysts; or by reduction of the oximes prepared from the aldehydes or ketones with hydroxylamine. The reduction of the oximes can be effected by means of hydrogen in the presence of metal catalysts, or by means of complex hydrides, such as $LiAlH_4$:

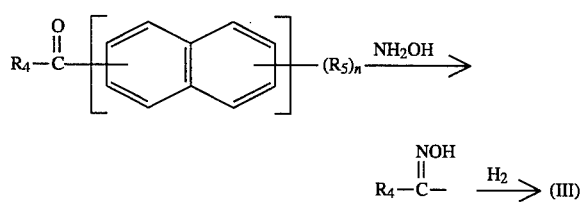

The naphthalene derivatives of formulae III and IV can also be obtained from aldehydes or ketones by reaction with ammonium formate and subsequent hydrolysis:

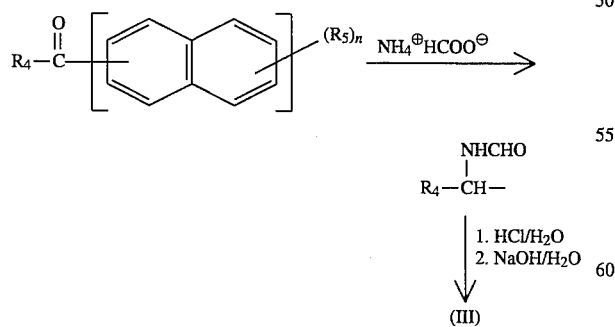

2) by reduction of nitriles or amides by means of hydrogen in the presence of metal catalysts or by means of complex hydrides, such as $LiAlH_4$:

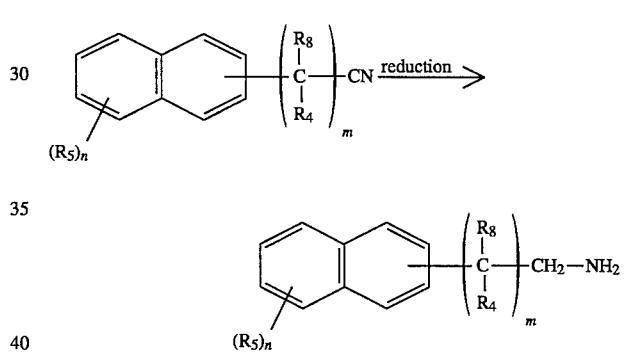

or

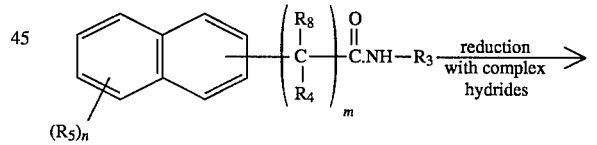

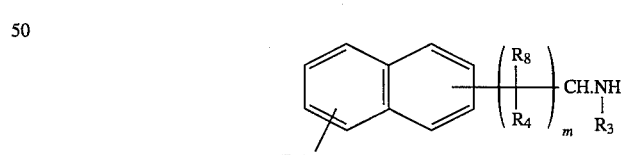

3) by reduction of nitro compounds with hydrogen and metal catalysts:

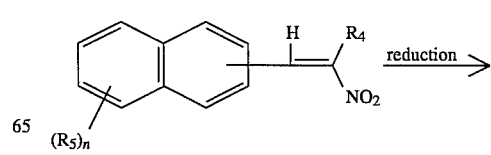

-continued

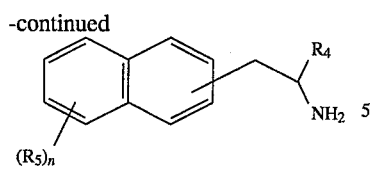

The present invention relates to the described preparation processes, including all subsidiary steps thereof.

The enantiomerically pure compounds of formula I can be prepared as follows:

1. by separating the racemic form of the compounds of formula I according to the generally known methods of racemate cleavage. This can be effected by reaction of the racemic compounds of formula I with an enantiomerically pure carboxylic acid or sulfo acid, such as tartaric acid, camphoric acid, camphorsulfonic acid, etc., to form the salts and subsequent fractional crystallisation of the diastereoisomeric salts. The enantiomerically pure compounds of formula I can then be freed again from the pure diastereoisomeric salts using bases;

2. by separating the racemic form of the compounds of formula I by chromatography, especially HPLC chromatography on a chiral carrier material, such as acetylcellulose, etc.;

3. by reacting the pyrimidines of formula II with enantiomerically pure amines of formula III or formula IV. Enantiomerically pure amines of formulae III and IV can be prepared analogously to the above-described methods or in accordance with generally known methods of enantioselective synthesis.

Compounds of formula I wherein $R_2$ is a thioalkyl radical are obtained by replacing $R_2$=halogen with mercaptans under basic conditions. They can be convened into the corresponding sulfones and sulfoxides by oxidation.

Surprisingly, it has been found that the compounds of formula I have, for practical purposes, a very advantageous biocidal spectrum against insects, pests of the order Acarina, and phytopathogenic microorganisms, especially fungi. Compounds of formula I have very advantageous curative, preventive and, in particular, systemic properties, and can be used for protecting numerous cultivated plants. With the compounds of formula I it is possible to inhibit or destroy the pests which occur in plants or in parts of plants (fruit, blossoms, leaves, stems, tubers, roots) in different crops of useful plants, while at the same time the parts of plants which grow later are also protected, for example, from attack by phytopathogenic microorganisms.

The compounds of formula I are effective, for example, against the phytopathogenic fungi belonging to the following classes: Fungi imperfecti (e.g. Botrytis, Pyricularia, Helminthosporium, Fusarium, Septoria, Cercospora and Alternaria); Basidiomycetes, (e.g. Rhizoctonia, Hemileia, Puccinia). They are also effective against the class of the Ascomycetes (e.g. Venturia and Erysiphe, Podosphaera, Monilinia, Uncinula) and of the Oomycetes (e.g. Phytophthora, Pythium, Plasmopara). The compounds of formula I can also be used as dressing agents for protecting seeds (fruit, tubers, grains) and plant cuttings against fungus infections as well as against phytopathogenic fungi which occur in the soil.

It has also been found that the compounds of formula I according to the invention are valuable active ingredients in the control of noxious insects and acarids which occur on useful plants and ornamentals in agriculture, especially in cotton, vegetable and fruit crops, in forestry, in the protection of stored goods and materiM stocks, and also in the hygiene sector, especially on domestic animals and productive livestock. They are effective against various development stages of these species. Their action may manifest itself in the death of the pests immediately or only at a later date, for example at moulting, or in markedly reduced oviposition and/or a markedly reduced hatching rate. The abovementioned pests include:

The order Lepidoptera (e.g. Chilo spp. and Heliothis spp.), the order Coleoptera (e.g. Anthonomus spp., Epilachna spp., *Leptinotarsa decemlineata*), the order Homoptera (e.g. *Bemisia tabaci*, Nephotettix spp., Nilaparvata spp.) and the order Acarina (e.g. Boophilus spp. and Tetranychus spp.). This list is not limiting.

The invention also relates to compositions comprising compounds of formula I as active ingredient, especially crop protection products, and to their use in the agricultural sector or related fields.

The present invention further embraces the preparation of those compositions, which comprises homogeneously mixing the active ingredient with one or more compounds or groups of compounds described herein. The invention furthermore relates to a method of treating plants, which comprises applying thereto the novel compounds of formula I or the novel compositions.

Target crops to be protected within the scope of the present invention comprise e.g. the following species of plants: cereals (wheat, barley, rye, oats, rice, maize, sorghum and related crops), beet (sugar beet and fodder beet), pomes, drupes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconut, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as tobacco, nuts, coffee, aubergines, sugar cane, tea, pepper, vines, hops, bananas and natural rubber plants, as well as ornamentals.

The compounds of formula I are normally applied in the form of compositions and can be applied to the crop area or plant to be treated, simultaneously or in succession, with further compounds. These further compounds can be fertilisers or micronutrient donors or other preparations that influence plant growth. They can also be selective herbicides, insecticides, fungitides, bactericides, nematicides, molluscicides or mixtures of several of these preparations, if desired together with further carriers, surfactants or other applicationpromoting adjuvants customarily employed in formulation technology.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

A preferred method of applying a compound of formula I, or an agrochemical composition which comprises at least one of said compounds, is foliar application. The number of applications and the rate of application depend on the risk of infestation by the corresponding pathogen. However, the compounds of formula I can also penetrate the plant through the roots via the soil (systemic action) if the locus of the plant is impregnated with a liquid formulation, or if the compounds are applied in solid form to the soil, e.g. in granular form (soil application). In paddy rice crops, such granules may be applied in metered amounts to the flooded flee field. The compounds of formula I may, however, also be applied to seeds (coating) either by impregnating the seeds with a liquid formulation of the active ingredient, or by coating them with a solid formulation.

The compounds of formula I are used in unmodified form or, preferably, together with the adjuvants conventionally employed in formulation technology, and are for this purpose advantageously formulated in known manner e.g. into emulsifiable concentrates, coatable pastes, directly sprayable or dilutable solutions, dilute emulsions, wettable powders, soluble powders, dusts, granules, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 5 g to 2 kg of active ingredient (a.i.) per hectare, preferably from 10 g to 1 kg a.i./ha, most preferably from 20 g to 600 g a.i./ha.

The formulations, i.e. the compositions, preparations or mixtures comprising the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used, e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are, for example, calcite or sand. In addition, a great number of pregranulated materials of inorganic nature can be used, e.g. especially dolomite or pulverised plant residues.

Depending on the nature of the compound of formula I to be formulated, suitable surface-active compounds are nonionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Representative examples of non-ionic surfactants are nonylphenolpolyethoxyethanols, castor oil polyglycol ethers, polypropylene/polyethylene oxide adducts, tributylphenoxypolyethyleneethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. Further surfactants customarily employed in formulation technology are known to the person skilled in the art or can be taken from the relevant specialist literature. The agrochemical compositions usually comprise 0.1 to 99%, preferably 0.1 to 95%, of a compound of formula I, 99.9 to 1%, preferably 99.8 to 5%, of a solid or liquid adjuvant, and 0 to 25%, preferably 0.1 to 25%, of a surfactant.

Whereas commercial products will preferably be formulated as concentrates, the end user will normally employ dilute formulations.

The compositions may also comprise further auxiliaries such as stabilisers, antifoams, viscosity regulators, binders, tackifiers as well as fertilisers or other active ingredients for obtaining special effects.

The following Examples serve to illustrate the invention in greater detail, but do not limit the invention.

Preparation Examples

EXAMPLE 1

Preparation of d,l-4-[1'-(β-naphthyl)-ethylamino]-5-chloro-6-ethyl-pyrimidine of the formula

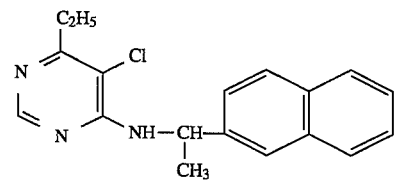

(comp. no. 1.2)

11.98 g of 1-(β-naphthyl)-1-aminoethane and 20 ml of triethylamine are added to a solution of 12.39 g of 4,5-dichloro-6-ethylpyrimidine in 150 ml of n-butanol. The mixture is boiled under reflux for 12 hours. After concentration of the reaction solution by evaporation, the crude product is dissolved in 20 ml of chloroform, 6 ml of concentrated hydrochloric acid are added, and the product is extracted by shaking with water. The organic phase is separated off and dried with sodium sulfate and the solvent is distilled off, yielding a light-brown oil. The oil is triturated with hexane, whereupon the desired end product crystallises out. Filtration yields 11.6 g of substance; m.p.: 80°–81 ° C.

The resulting racemate can be separated into a (+)-enantiomer and its biologically more active (−)-enantiomer by fractional crystallisation with, for example, optically active tartaric acid, or can be resolved by separation on a chiral column by means of HPLC.

EXAMPLE 2

Preparation of
(d,l)-4-[1'-(2-(6-methoxynaphthyl))-propylamino]-5-chloro-6-ethylpyrimidine

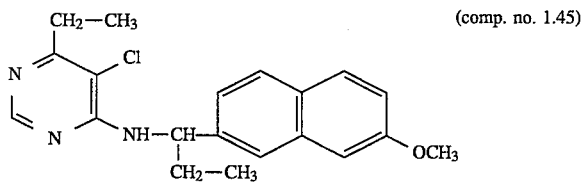

(comp. no. 1.45)

2.1 g of 1-(2-(6-methoxynaphthyl))-1-aminopropane, 2.1 g of 4,5-dichloro-6-ethylpyrimidine and 1.3 g of triethylamine are introduced into 50 ml of n-butanol. The solution is heated under reflux for 12 hours. The solvent is then largely evaporated off, water is added to the residue, and the product is extracted with ethyl acetate. The solution is dried over $Na_2SO_4$ and concentrated. The residue is chromatographed through a short column on silica gel with ethyl acetate/hexane (1:1). Yield: 2.4 g (resin).

EXAMPLE 2a

Preparation of
2-(6-methoxynaphthyl)-ethylketoxime

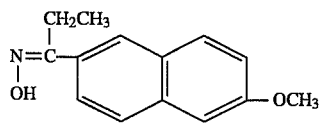

21.4 g of 6-methoxy-2-propionylnaphthalene are dissolved in 100 ml of ethanol. 7.7 g of hydroxyammonium chloride and 9.5 g of pyridine are added to that solution, and the mixture is then boiled under reflux for approximately 12 hours. After cooling, the solvent is distilled off using a rotary evaporator, and the residue is taken up in water and extracted with ethyl acetate. After the ethyl acetate extract has been washed with water and brine, it is dried over $Na_2SO_4$, filtered and concentrated using a rotary evaporator. The residue is recrystallised from cyclohexane. Yield: 18.4 g, m.p. 161°–162° C.

EXAMPLE 2b

Preparation of
1'-[2-(6-methoxynaphthyl)]-propylamine

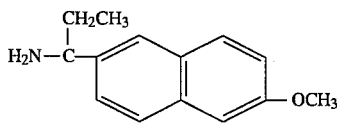

7.4 g of 2-(6-methoxynaphthyl)-ethylketoxime are hydrogenated with hydrogen in 100 ml of methanol and 6 g of ammonia (liquid), with the addition of 0.7 g of Raney nickel, at 60°–70° C. and under a pressure of $10^7$ Pa, until the reaction ceases. The catalyst is filtered off over Hyflo and then washed with methanol. The methanol is evaporated off under reduced pressure using a rotary evaporator, and the residue is taken up in methylene chloride and washed with water. The solution is dried over $Na_2SO_4$ and then filtered, and the solvent is then evaporated off. The residue is recrystallised from diethyl ether/hexane. Yield: 5.6 g; m.p. 61°–62° C.

EXAMPLE 3

Preparation of
(d,l)-4-[1'-(2-(1-difluoromethoxynaphthyl))-ethylamino]-5-chloro-6-ethylpyrimidine

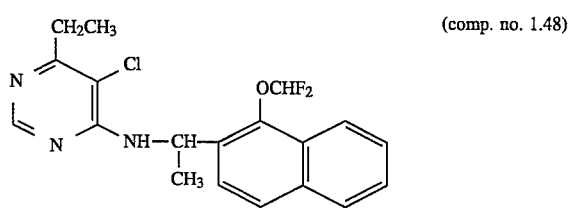

(comp. no. 1.48)

2.1 g of methyl-2-(1-difluoromethoxynaphthyl)-methylamine, 1.6 g of 4,5-dichloro-6-ethylpyrimidine and 1.2 g of triethylamine are added to 20 ml of n-butanol. The solution is kept at 100° C. for approximately 12 hours. Then the solvent is largely evaporated off in vacuo using a rotary evaporator, water is added to the residue, and the mixture is extracted several times with ethyl acetate. The ethyl acetate solution is dried over $Na_2SO_4$ and concentrated by evaporation. The oil that remains is chromatographed on silica gel with ethyl acetate/hexane (3:1) as eluant. Yield: 1.4 g of oil.

EXAMPLE 3a

Preparation of
1-difluoromethoxy-2-acetylnaphthalene

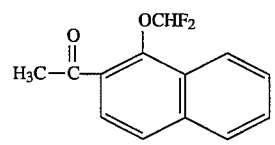

10 g of 1-hydroxy-2-acetylnaphthalene are dissolved in 60 ml of dioxane, and 30 ml of 30% sodium hydroxide solution are added. At a temperature of from 70° C. to 80° C., difluorochloromethane (Freon 22) is introduced until no further absorption is observed. The dioxane phase is then decanted, the NaOH phase is washed with dioxane, the dioxane phase is decanted, and the combined dioxane solutions are largely concentrated in vacuo using a rotary evaporator. Water is added to the residue, the mixture is extracted several times with diethyl ether, and the diethyl ether solution is dried over $Na_2SO_4$, filtered and concentrated by evaporation. The residue is recrystallised from diethyl ether/hexane. Yield: 4 g, m.p. 80°–81° C.

EXAMPLE 3b

Preparation of
N-formyl-1'-[2-(1-difluoromethoxynaphthyl)]-
ethylamine

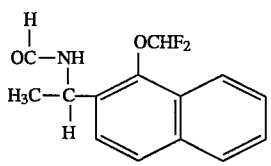

10.3 g of 1-difluoromethoxy-2-acetylnaphthalene are added in portions to 20 g of formamide, which has been heated to 150° C., with the simultaneous dropwise addition of 5 g of formic acid. The mixture is then stirred overnight (approximately 12 hours) at that temperature. After cooling, water is added and the product is extracted with ethyl acetate. After the ethyl acetate phase has been washed several times with water, it is dried over $Na_2SO_4$ and concentrated in vacuo using a rotary evaporator. The oily residue is chromatographed on silica gel with ethyl acetate/hexane (3:1) as eluant. Yield: 5.4 g of oil.

EXAMPLE 3c

Preparation of
1'-[2-(1-difluoromethoxynaphthyl)]-ethylamine

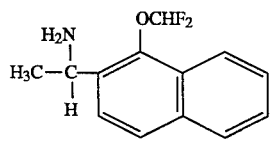

40 ml of ethanol/water (1:1) are added to 5.4 g of N-formyl-1-(2-(1-difluoromethoxynaphthyl))-ethylamine, 1.8 g of potassium hydroxide pellets are added, and the mixture is then boiled under reflux for 6 hours. Ethanol is then largely evaporated off using a rotary evaporator, and the aqueous residue is extracted several times with diethyl ether. The diethyl ether solution is dried over $Na_2SO_4$ and concentrated using a rotary evaporator. The resulting oily residue is used directly without purification. Yield: 4.1 g.

EXAMPLE 4

Preparation of
4-[1'-(β-naphthyl)-ethylamino]-5-nitro-6-ethyl-
pyrimidine

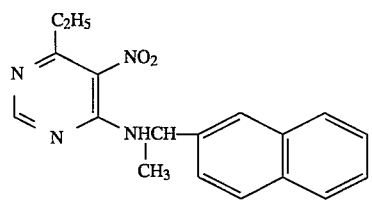

[comp. no. 1.80]

1.87 g (0.01 mol) of 4-chloro-5-nitro-6-ethylpyrimidine are dissolved with 1.52 g (0.015 mol) of triethylamine in 15 ml of tetrahydrofuran, and 1.97 g (0.0115 mol) of 1-(b-naphthyl)-1-aminoethane are added dropwise with cooling at a maximum of 50° C. After one hour, the mixture is extracted with water and ethyl acetate. Concentration of the extract yields 3.85 g of crude product, which is purified by means of column chromatography on silica gel (eluant: 10 parts ethyl acetate and 90 parts hexane). The yield is 2.75 g (85% of the theoretical yield) of colourless oil.

EXAMPLE 4a

Preparation of 4-hydroxy-5-nitro-6-ethylpyrimidine

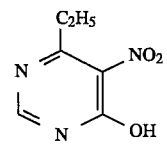

8 ml of 25% oleum are added dropwise with cooling at a maximum of 10° C. to 8 ml of 100% nitric acid. 12.4 g (0.10 mol) of 4-hydroxy-6-ethylpyrimidine are then introduced in portions at a maximum of 35° C. The temperature is kept at 40° C. overnight. For the purpose of reacting further any starting material that remains, a further 13 ml of 25% oleum and 11 ml of 100% nitric acid are added dropwise at a maximum of 40° C. The mixture is left for 12 hours at 40° C. to complete the reaction and is then poured carefully onto ice and extracted completely with ethyl acetate, and the extracts are washed with sodium hydrogen carbonate solution. The extract is concentrated using a rotary evaporator, whereupon 11.8 g (69.7% of the theoretical yield) of pure substance crystallise out; m.p. 181°–183° C.

EXAMPLE 4b

Preparation of 4-chloro-5-nitro-6-ethylpyrimidine

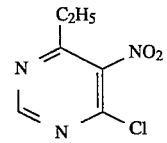

18.7 g (0.125 mol) of diethylaniline are dissolved in 18 ml of phosphorus chloride, and then 8.46 g (0.05 mol) of 4-hydroxy-5-nitro-6-ethylpyrimidine are stirred in. During the addition, the temperature rises from 22° to 47° C. A solution is formed which is heated at 60° C. for 2 hours. It is then stirred with ice-water and ethyl acetate for 30 minutes for the purpose of hydrolysis. The organic phase is separated off and combined with the extracts obtained by extraction, and the mixture is washed with $NaHCO_3$ solution. Removal of the solvent yields 9.1 g of crude product, which is purified by column chromatography on silica gel (eluant:ethyl acetate/hexane 20:80 parts). 6.76 g (72.1% of the theoretical yield) of pure product are obtained in the form of an oil.

EXAMPLE 5

Preparation of 4-[1'-(β-naphthyl)-ethylamino]-5-methylthio-6-ethyl-pyrimidine

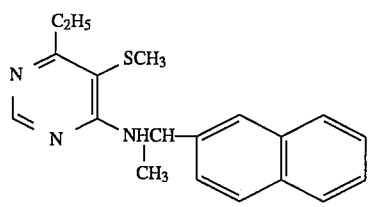

(comp. no. 1.61)

4.99 g (0.014 mol) of 4-[1'-(β-naphthyl)-ethylamino]-5-bromo-6-ethylpyrimidine are dissolved in 18 ml of N-methylpyrrolidone, and the solution is heated at 60° C. with 3.2 g of sodium methanethiolate ($CH_3SNa$) for 5 hours. The mixture is then extracted with water and ethyl acetate, the extract is washed and the solvent is removed using a rotary evaporator. Purification by chromatography on silica gel (eluant: 3 parts ethyl acetate and 7 parts hexane) yields, in addition to the starting product, 1.42 g of pure substance in the form of a colourless oil. Analysis: $C_{19}H_{21}N_3S$ (M=323.46).

|     | calculated | found |
| --- | --- | --- |
| % N | 12.99 | 12.96 |
| % S | 9.91  | 10.34 |

EXAMPLE 6a

Preparation of 4-chloro-6-ethylpyrimidine

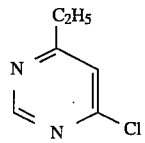

12.4 g (0.10 mol) of 4-hydroxy-6-ethylpyrimidine, prepared according to EP 326 389, are introduced into 25 ml of phosphorus oxychloride, the temperature rising spontaneously to 70° C. A clear solution is formed, which is kept at 70° C. for a further 2 hours and, after cooling, is stirred into ice-water. Extraction with ether yields 12.0 g of liquid crude product which is distilled in a bulb tube at 105° C. under a pressure of 26 mbar to give 11.0 g of pure substance. Analysis: $C_6H_7ClN_2$ (M=142.59).

|     | calculated | found |
| --- | --- | --- |
| % C | 50.54 | 50.43 |
| % H | 4.95  | 4.89 |
| % N | 19.65 | 19.86 |
| % Cl | 24.86 | 24.79 |

EXAMPLE 6b

Preparation of 4-hydroxy-5-bromo-6-ethylpyrimidine

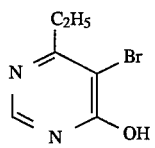

24.8 g (0.20 mol) of 4-hydroxy-6-ethylpyrimidine are dissolved with 16.8 g (0.20 mol) of sodium hydrogen carbonate in 50 ml of water, and 32 g (0.20 mol) of bromine are slowly added dropwise at 8° to 10° C., with cooling. In the course of the addition, carbon dioxide evolves, and the product precipitates in the form of crystals. The product is separated off by extraction with ethyl acetate and crystallises out when the extract is concentrated using a rotary evaporator. There are obtained 22.7 g (55.9% of the theoretical yield) of a first fraction having a melting point of 177°–179° C. Concentration of the mother liquor yields a further 3.5 g (8.6%); m.p. 175°–177° C.

EXAMPLE 6c

Preparation of 4-chloro-5-bromo-6-ethylpyrimidine

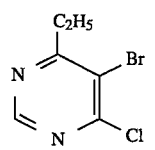

29.7 g (0.146 mol) of 4-hydroxy-5-bromo-6-ethylpyrimidine are introduced slowly into 27.3 g (0.178 mol) of phosphorus oxychloride. The suspension dissolves on heating to 70° C.; the reaction is slightly exothermic. The temperature is kept at 70° C. for 1½ hours and, after cooling, the solution is poured onto ice-water and neutralised carefully to pH 5–7, at 0° C., with 30% sodium hydroxide solution. Extraction with ethyl acetate yields, after removal of the solvent, 30.4 g of crude product. Distillation yields 23.9 g (73.9% of the theoretical yield) of pure substance having a boiling point of 112°–114° C./24 mbar.

EXAMPLE 6d

Preparation of 4-hydroxy-5-iodo-6-ethylpyrimidine

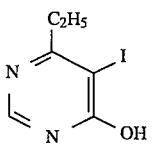

50.8 g of iodine (0.20 mol) are introduced into 850 ml of acetic acid, and 14.8 g (0.21 mol) of chlorine are introduced at 30°–33° C., whereupon the iodine dissolves. 49.7 g (0.4 mol) of 4-hydroxy-6-ethylpyrimidine in solution in 150 ml of acetic acid are then added dropwise at 20° C., the crystalline end product separating out. Filtration with suc-

EXAMPLE 6e

Preparation of 4-chloro-5-iodo-6-ethylpyrimidine

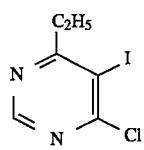

21.7 g (0.087 mol) of 4-hydroxy-5-iodo-6-ethylpyrimidine are stirred into 50 ml of phosphorus oxychloride which has been heated to 60° C., a slightly exothermic reaction taking place. The temperature is kept constant at 60° C. and the mixture is left for one hour to complete the reaction. The mixture is then poured onto ice-water and stirred for 30 minutes in order to hydrolyse completely the excess phosphorus oxychloride. Extraction with ethyl acetate yields 23.5 g of crystalline crude product. Recrystallisation from a mixture of 1 part ethyl acetate and 10 parts hexane yields 18.8 g (80.7% of the theoretical yield) of pure substance; m.p. 56°–57° C.

EXAMPLE 6f

Preparation of 4,5-dichloro-6-isopropylpyrimidine

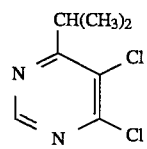

N-butyl lithium (1.6 mol solution in hexane, 19.4 ml) is added dropwise at 0° C., under a nitrogen atmosphere, to a solution of diisopropylamine (4.4 ml) in tetrahydrofuran (100 ml), and the mixture is stirred for 20 minutes. The solution is cooled to −78° C. and then 5 g of 4,5-dichloro-6-ethylpyrimidine in solution in 10 ml of tetrahydrofuran are added dropwise. The mixture is stirred at −78° C. for one hour and then brought to room temperature over a period of 2 hours. After the addition of water (200 ml), the mixture is extracted with ethyl acetate and the organic phase is dried over sodium sulfate and concentrated. Chromatography on silica gel (eluant: ethyl acetate/hexane 1:10) yields 3.8 g (71% of the theoretical yield) of 4,5-dichloro-6-isopropylpyrimidine in the form of a yellow oil.

H-NMR: 8.79 (1H, s), 3.58 (1H, septett), 1.3 (6H, d)

The following compounds can be prepared in this manner or in accordance with one of the methods described above.

TABLE 1

β-Naphthyl derivatives

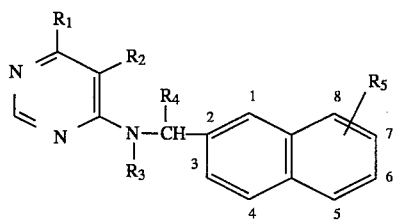

| Comp No. | $R_1$ | $R_2$ | $R_4$ | $R_3$ | $R_5$ | Physical data |
|---|---|---|---|---|---|---|
| 1.1 | $C_2H_5$ | Cl | H | H | H | m.p. 127–128° C. |
| 1.2 | $C_2H_5$ | Cl | $CH_3$ | H | H | m.p. 80–81° C. |
| 1.3 | $C_2H_5$ | Cl | $C_2H_5$ | H | H | $n_D^{20}$ 1.6119 |
| 1.4 | $C_2H_5$ | Cl | Cyclopropyl | H | H | |
| 1.5 | $C_2H_5$ | Cl | $CH_3$ | $CH_3$ | H | $n_D^{20}$ 1.6245 |
| 1.6 | $C_2H_5$ | Cl | $C_2H_5$ | $CH_3$ | H | |
| 1.7 | $C_2H_5$ | Cl | $C_2H_5$ | $-COCH_3$ | H | |
| 1.8 | $C_2H_5$ | Cl | $C_2H_5$ | $-S-C_6H_4Cl(4)$ | H | |
| 1.9 | $C_2H_5$ | Cl | $C_2H_5$ | H | 6-Br | $n_D^{20}$ 1.6238 |
| 1.10 | $C_2H_5$ | Cl | $C_2H_5$ | H | $6-O-C_6H_5$ | |
| 1.11 | $CH=CH_2$ | Cl | $CH_3$ | H | H | |
| 1.12 | $CH=CH_2$ | Cl | $C_2H_5$ | H | H | |
| 1.13 | $CF_3$ | Cl | $CH_3$ | H | H | m.p. 101–102° C. |
| 1.14 | $CF_3$ | Cl | $C_2H_5$ | H | H | |
| 1.15 | Cyclopropyl | Cl | H | H | H | |
| 1.16 | Cyclopropyl | Cl | $CH_3$ | H | H | resin |
| 1.17 | Cyclopropyl | Cl | $C_2H_5$ | H | H | |
| 1.18 | F | $C_2H_5$ | $CH_3$ | H | H | resin |
| 1.19 | Cl | $C_2H_5$ | $CH_3$ | H | H | m.p. 102–103° C. |
| 1.20 | $C_2H_5$ | $NO_2$ | $C_2H_5$ | H | H | |
| 1.21 | $C_2H_5$ | CN | $C_2H_5$ | H | H | |
| 1.22 | $C_2H_5$ | Cl | $C_2H_5$ | −CO-2-furyl | H | |
| 1.23 | $C_2H_5$ | Cl | $C_2H_5$ | $-S-C(CH_3)_2-CN$ | H | |

TABLE 1-continued

β-Naphthyl derivatives

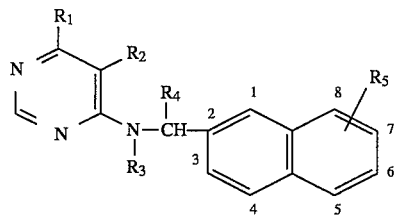

| Comp No. | R₁ | R₂ | R₄ | R₃ | R₅ | Physical data |
|---|---|---|---|---|---|---|
| 1.24 | C₂H₅ | Cl | C₂H₅ | —COCH₃ | 6-Br | |
| 1.25 | —CH₂Cl | Cl | C₂H₅ | H | H | |
| 1.26 | —CH₂OCH₃ | Cl | C₂H₅ | H | H | |
| 1.27 | C₂H₅ | Br | C₂H₅ | H | H | |
| 1.28 | C₂H₅ | F | C₂H₅ | H | H | |
| 1.29 | F | C₂H₅ | C₂H₅ | H | H | |
| 1.30 | Cl | C₂H₅ | C₂H₅ | H | H | |
| 1.31 | Br | C₂H₅ | C₂H₅ | H | H | |
| 1.32 | C₂H₅ | Cl | CH₃ | —S—C₆H₄—NO₂(4) | H | |
| 1.33 | C₂H₅ | Cl | CH₃ | —S—C₆H₄—NO₂(2) | H | |
| 1.34 | C₂H₅ | Cl | CH₃ | H | 4-Br | |
| 1.35 | C₂H₅ | Cl | CH₃ | H | 6-OCH₃ | m.p. 99–101° C. |
| 1.36 | C₂H₅ | Cl | CH₃ | H | 6-O—C₆H₄Cl(4) | |
| 1.37 | C₂H₅ | Cl | CH₃ | H | 1-CH₃ | |
| 1.38 | C₂H₅ | Cl | CH₃ | H | 8-Cl | |
| 1.39 | C₂H₅ | Cl | CH₃ | H | 1,4-di-Br | |
| 1.40 | C₂H₅ | Cl | CH₃ | H | 6-SCH₃ | |
| 1.41 | C₂H₅ | Cl | CH₃ | H | 1-Br | |
| 1.42 | C₂H₅ | Cl | CH₃ | H | 1-OH | |
| 1.43 | C₂H₅ | Cl | CH₃ | H | 1-OCH₃ | resin |
| 1.44 | C₂H₅ | Cl | CH₃ | H | 6-CH₃ | m.p. 94–95° C. |
| 1.45 | C₂H₅ | Cl | C₂H₅ | H | 6-OCH₃ | resin |
| 1.46 | C₂H₅ | Cl | C₂H₅ | —S—CCl₃ | H | |
| 1.47 | C₂H₅ | Cl | C₂H₅ | —S—CCl₂F | H | |
| 1.48 | C₂H₅ | Cl | CH₃ | H | 1-OCHF₂ | oil |
| 1.49 | C₂H₅ | Cl | CH₃ | H | 6-OCHF₂ | |
| 1.50 | C₂H₅ | Cl | C₂H₅ | H | 6-OCHF₂ | |
| 1.51 | C₂H₅ | Cl | CH₃ | H | 6-OCH₃, 7-Br | |
| 1.52 | CH₃ | Cl | CH₃ | H | 6-OCHF₂ | |
| 1.53 | CH₃ | Cl | CH₃ | H | H | oil |
| 1.54 | CH₃ | Cl | CH₃ | H | 6-OCH₃ | |
| 1.55 | CH₃ | Cl | C₂H₅ | H | 6-OCH₃ | oil |
| 1.56 | CH₃ | Cl | CH₃ | H | 6-CH₃ | oil |
| 1.57 | CH₃ | Cl | CH₃ | H | 6-Br | m.p. 124–125° C. |
| 1.58 | CH₃ | Cl | CH₃ | H | 1-OCH₃ | oil |
| 1.59 | CH₃ | Cl | CH₃ | H | 1-Br | |
| 1.60 | CH₃ | Cl | CH₃ | H | 6-OCHF₂ | |
| 1.61 | C₂H₅ | SCH₃ | CH₃ | H | H | oil |
| 1.62 | C₂H₅ | SOCH₃ | CH₃ | H | H | |
| 1.63 | C₂H₅ | SO₂CH₃ | CH₃ | H | H | |
| 1.64 | C₂H₅ | SCH₃ | CH₃ | H | 6-CH₃ | |
| 1.65 | C₂H₅ | SOCH₃ | CH₃ | H | 6-CH₃ | |
| 1.66 | C₂H₅ | SO₂CH₃ | CH₃ | H | 6-CH₃ | |
| 1.67 | C₂H₅ | SCH₃ | CH₃ | H | 6-OCH₃ | |
| 1.68 | C₂H₅ | SO₂CH₃ | CH₃ | H | 6-OCH₃ | |
| 1.69 | C₂H₅ | Cl | Cyclopropyl | H | 6-CH₃ | |
| 1.70 | C₂H₅ | Cl | Cyclopropyl | H | 6-OCH₃ | resin |
| 1.71 | C₂H₅ | Cl | Cyclopropyl | H | 6-Br | |
| 1.72 | C₂H₅ | Cl | CH₃ | H | H | (+)form, oil $[\alpha]_D^{20} = +6.13°$ |
| 1.73 | C₂H₅ | Cl | CH₃ | H | H | (−)form, oil $[\alpha]_D^{20} = -6.01°$ |
| 1.74 | C₂H₅ | Cl | -n-Propyl | H | H | |
| 1.75 | C₂H₅ | Cl | -n-Butyl | H | H | |
| 1.76 | C₂H₅ | Cl | -i-Propyl | H | H | m.p. 81–82° C. |
| 1.77 | Cl | NH₂ | CH₃ | H | H | m.p. 124–126° C. |
| 1.78 | Cl | H | CH₃ | H | H | m.p. 113–114° C. |
| 1.79 | C₂H₅ | H | CH₃ | H | H | m.p. 83–84° C. |
| 1.80 | C₂H₅ | NO₂ | CH₃ | H | H | oil |
| 1.81 | Cl | NO₂ | CH₃ | H | H | m.p. 82–83° C. |
| 1.82 | C₂H₅ | NH₂ | CH₃ | H | H | m.p. 146–147° C. |
| 1.83 | C₂H₅ | NHCH₃ | CH₃ | H | H | |

TABLE 1-continued

β-Naphthyl derivatives

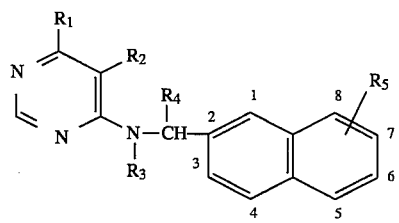

| Comp No. | $R_1$ | $R_2$ | $R_4$ | $R_3$ | $R_5$ | Physical data |
|---|---|---|---|---|---|---|
| 1.84 | $C_2H_5$ | Br | $CH_3$ | H | H | m.p. 62–63° C. |
| 1.85 | $C_2H_5$ | $OCH_3$ | $CH_3$ | H | H | |
| 1.86 | $n-C_3H_7$ | Cl | $CH_3$ | H | H | oil |
| 1.87 | $n-C_3H_7$ | $NO_2$ | $CH_3$ | H | H | |
| 1.88 | $n-C_3H_7$ | $NH_2$ | $CH_3$ | H | H | |
| 1.89 | $n-C_3H_7$ | Br | $CH_3$ | H | H | oil |
| 1.90 | $CH_3$ | Br | $CH_3$ | H | H | m.p. 90–91° C. |
| 1.91 | $CH_3$ | $NO_2$ | $CH_3$ | H | H | |
| 1.92 | $CH_3$ | $NH_2$ | $CH_3$ | H | H | |
| 1.93 | H | Cl | $CH_3$ | H | H | |
| 1.94 | H | Cl | $C_2H_5$ | H | H | |
| 1.95 | H | Cl | $CH_3$ | H | 6-$CH_3$ | |
| 1.96 | H | Cl | $CH_3$ | H | 6-$OCH_3$ | |
| 1.97 | H | Br | $CH_3$ | H | H | |
| 1.98 | H | $NH_2$ | $CH_3$ | H | H | |
| 1.99 | H | $NO_2$ | $CH_3$ | H | H | |
| 1.100 | $C_2H_5$ | I | $CH_3$ | H | H | oil |
| 1.101 | $CH_3$ | I | $CH_3$ | H | H | oil |
| 1.102 | $n-C_3H_7$ | I | $CH_3$ | H | H | |
| 1.103 | $C_2H_5$ | F | $CH_3$ | H | H | |
| 1.104 | $CH_3$ | F | $CH_3$ | H | H | |
| 1.105 | $n-C_4H_9$ | Cl | $CH_3$ | H | H | |
| 1.106 | $CH_3$ | H | $CH_3$ | H | H | m.p. 118–119° C. |
| 1.107 | $n-C_3H_7$ | H | $CH_3$ | H | H | m.p.133–134° C. |
| 1.108 | $C_2H_5$ | $SC_2H_5$ | $CH_3$ | H | H | oil |
| 1.109 | $CH_3$ | $SC_3H_7(n)$ | $CH_3$ | H | H | |
| 1.110 | $n-C_3H_7$ | $SCH_3$ | $CH_3$ | H | H | |
| 1.111 | $CH_3$ | $CH_3$ | $CH_3$ | H | H | m.p. 81–82° C. |
| 1.112 | $C_2H_5$ | $CH_3$ | $CH_3$ | H | H | |
| 1.113 | $n-C_3H_7$ | $CH_3$ | $CH_3$ | H | H | |
| 1.114 | $C_2H_5$ | $C_2H_5$ | $CH_3$ | H | H | |
| 1.115 | $C_2H_5$ | $n-C_3H_7$ | $CH_3$ | H | H | |
| 1.116 | $n-C_4H_9$ | $NO_2$ | $CH_3$ | H | H | |
| 1.117 | —C≡$CCH_3$ | H | $CH_3$ | H | H | |
| 1.118 | —C≡$CCH_3$ | Cl | $CH_3$ | H | H | |
| 1.119 | $CH_2OCH_3$ | Cl | $CH_3$ | H | H | |
| 1.120 | $CH_2OC_2H_5$ | Cl | $CH_3$ | H | H | |
| 1.121 | $CH_2SCH_3$ | Cl | $CH_3$ | H | H | |
| 1.122 | $CH_2SC_2H_5$ | Cl | $CH_3$ | H | H | |
| 1.123 | $CH_2SOCH_3$ | Cl | $CH_3$ | H | H | |
| 1.124 | $CH_2SO_2CH_3$ | Cl | $CH_3$ | H | H | |
| 1.125 | $C_2H_5$ | $NHCOCH_3$ | $CH_3$ | H | H | |
| 1.126 | $C_2H_5$ | $N=CHC(CH_3)_2$ | $CH_3$ | H | H | |
| 1.127 | $C_2H_5$ | $NHCH_2CH(CH_3)_2$ | $CH_3$ | H | H | |
| 1.128 | $C_2H_5$ | $NHC_2H_5$ | $CH_3$ | H | H | |
| 1.129 | H | $C_2H_5$ | $CH_3$ | H | H | m.p. 117–118° C. |
| 1.130 | $C_2H_5$ | Cl | $CH_3$ | H | 6-Cl | m.p. 86–87° C. |
| 1.131 | $C_2H_5$ | Cl | $C_2H_5$ | H | 6-Cl | |
| 1.132 | $CH_3$ | Cl | i-Propyl | H | H | m.p. 106–107° C. |
| 1.133 | $C_2H_5$ | Cl | $CH_3$ | H | 1-$OCH_3$, 4-Cl | m.p. 101–102° C. |
| 1.134 | $CH_3$ | Cl | $CH_3$ | H | 1-$OCH_3$, 4-Cl | |
| 1.135 | $CF_3$ | Cl | $CH_3$ | H | 1-$OCH_3$, 4-Cl | |
| 1.136 | $CF_3$ | Cl | $CH_3$ | H | 6-Cl | |
| 1.137 | $CF_3$ | Br | $CH_3$ | H | 6-Cl | |
| 1.138 | $CF_3$ | Cl | $C_2H_5$ | H | 6-Cl | |
| 1.139 | $CF_3$ | Cl | $CH_3$ | H | 6-Br | |
| 1.140 | $CF_3$ | Cl | $CH_3$ | H | 6-$OCH_3$ | |
| 1.141 | $CF_3$ | Cl | $C_2H_5$ | H | 6-$OCH_3$ | |
| 1.142 | $CF_3$ | Cl | $CH_3$ | H | 6-$CH_3$ | |
| 1.143 | $CF_3$ | Cl | $CH_3$ | H | 1-$OCH_3$ | |
| 1.144 | $CF_3$ | Cl | $CH_3$ | H | 1-$OCHF_2$ | |

TABLE 1-continued

β-Naphthyl derivatives

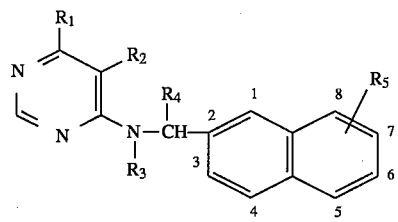

| Comp No. | R₁ | R₂ | R₄ | R₃ | R₅ | Physical data |
|---|---|---|---|---|---|---|
| 1.145 | CF₃ | Cl | n-Propyl | H | H | |
| 1.146 | CF₃ | Cl | i-Propyl | H | H | |
| 1.147 | C₂H₅ | Cl | CH₃ | H | 1-Br | |
| 1.148 | CH₃ | Cl | CH₃ | H | 1-OCHF₂ | oil |
| 1.149 | C₂H₅ | Cl | CH₃ | H | 6-Br | m.p. 61–63° C. |
| 1.150 | C₂H₅ | Br | CH₃ | H | 6-Br | resin |
| 1.151 | C₂H₅ | Br | CH₃ | H | 6-CH₃ | resin |
| 1.152 | CH₃ | Cl | CH₃ | H | 3-OCH₃, 7-Br | m.p. 119–120° C. |
| 1.153 | H | CH₃ | CH₃ | H | H | m.p. 110–111° C. |
| 1.154 | C₂H₅ | Br | C₂H₅ | H | 6-OCH₃ | resin |
| 1.155 | C₂H₅ | I | CH₃ | H | 6-CH₃ | oil |
| 1.156 | CF₃ | H | CH₃ | H | H | |
| 1.157 | Cl | Cl | CH₃ | H | H | |
| 1.158 | Cl | Br | Ch₃ | H | H | |
| 1.159 | Cl | I | CH₃ | H | H | |
| 1.160 | Cl | F | CH₃ | H | H | |
| 1.161 | CH₂OCH₃ | Br | CH₃ | H | H | oil |
| 1.162 | CH₂OCH₃ | I | CH₃ | H | H | |
| 1.163 | Cl | Cl | CH₃ | H | 6-Br | |
| 1.164 | Cl | Br | Ch₃ | H | 6-Br | |
| 1.165 | Cl | I | CH₃ | H | 6-Br | |
| 1.166 | CH₂OCH₃ | Cl | CH₃ | H | 6-Br | |
| 1.167 | CH₂OCH₃ | Br | CH₃ | H | 6-Br | |
| 1.168 | CH₂OCH₃ | I | CH₃ | H | 6-Br | |
| 1.169 | CH₂SCH₃ | Br | CH₃ | H | H | |
| 1.170 | CH₂SCH₃ | I | CH₃ | H | H | |
| 1.171 | C₂H₅ | Cl | CH₃ | COCH₃ | H | |
| 1.172 | C₂H₅ | Br | CH₃ | COCH₃ | H | |
| 1.173 | C₂H₅ | I | CH₃ | COCH₃ | H | |
| 1.174 | CH₃ | Cl | CH₃ | COC₂H₅ | H | |
| 1.175 | CH₃ | Br | CH₃ | COCH₃ | H | |
| 1.176 | n-C₃H₇ | Cl | CH₃ | COCH₃ | H | |
| 1.177 | CH(CH₃)₂ | Cl | CH₃ | H | H | |
| 1.178 | CH(CH₃)₂ | Br | CH₃ | H | H | |
| 1.179 | CH(CH₃)₂ | I | CH₃ | H | H | |
| 1.180 | n-C₅H₁₁ | Cl | CH₃ | H | H | |
| 1.181 | C₂H₅ | Cl | CH₃ | H | 6-F | |
| 1.182 | C₂H₅ | Br | CH₃ | H | 6-F | |
| 1.183 | CH₃ | Cl | CH₃ | H | 6-F | |
| 1.184 | CH₃ | Br | CH₃ | H | 6-F | |
| 1.185 | CH₃ | I | CH₃ | H | 6-F | |
| 1.186 | C₂H₅ | C₂H₅ | CH₃ | H | 6-F | |
| 1.187 | C₂H₅ | C₂H₅ | CH₃ | H | 6-Cl | |
| 1.188 | CH₃ | Cl | n-C₃H₇ | H | H | oil |
| 1.189 | CH₃ | Cl | H | H | H | m.p. 102° C. |
| 1.190 | n-C₃H₇ | Cl | CH₃ | H | 6-Br | m.p. 75–76° C. |
| 1.191 | —CH(CH₃)C₂H₅ | Cl | CH₃ | H | H | m.p. 92–93° C. |
| 1.192 | —CH(CH₃)C₂H₅ | Br | CH₃ | H | H | |
| 1.193 | C(CH₃)=CH—CH₃ | Cl | CH₃ | H | H | |
| 1.194 | —C(CH₃)=CH—CH₃ | Br | CH₃ | H | H | |
| 1.195 | —CH(CH₃)CH₂CH=CH₂ | Cl | CH₃ | H | H | oil |
| 1.196 | —CH(CH₃)CH₂C≡CH | Cl | CH₃ | H | H | |
| 1.197 | —CHCl—CH₃ | Cl | CH₃ | H | H | m.p. 115–116° C. |
| 1.198 | —CHBr—CH₃ | Cl | CH₃ | H | H | |
| 1.199 | —CHF—CH₃ | Cl | CH₃ | H | H | |
| 1.200 | —CH(CH₃)—SCH₃ | Cl | CH₃ | H | H | oil |
| 1.201 | —CH(CH₃)—SOCH₃ | Cl | CH₃ | H | H | |
| 1.202 | —CH(CH₃)—SO₂CH₃ | Cl | CH₃ | H | H | oil |
| 1.203 | —C≡CH | Cl | CH₃ | H | H | |
| 1.204 | —C≡CH | Br | CH₃ | H | H | |

TABLE 1-continued

β-Naphthyl derivatives

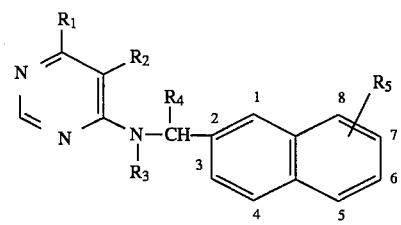

| Comp No. | $R_1$ | $R_2$ | $R_4$ | $R_3$ | $R_5$ | Physical data |
|---|---|---|---|---|---|---|
| 1.205 | —C≡CH | Cl | —$C_2H_5$ | H | H | |
| 1.206 | —$CF_2CH_3$ | Cl | $CH_3$ | H | H | |
| 1.207 | —$C(CH_3)_3$ | Cl | $CH_3$ | H | H | |
| 1.208 | $C_2H_5$ | Br | n-Propyl | H | H | oil |
| 1.209 | $C_2H_5$ | I | $CH_3$ | H | 6-Br | oil |

TABLE 2

α-Naphthyl derivatives

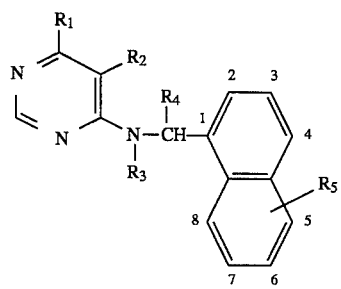

| Comp No. | $R_1$ | $R_2$ | $R_4$ | $R_3$ | $R_5$ | Physical data |
|---|---|---|---|---|---|---|
| 2.1 | $C_2H_5$ | Cl | H | H | H | m.p. 96–98° C. |
| 2.2 | $C_2H_5$ | Cl | $CH_3$ | H | H | m.p. 97–99° C. |
| 2.3 | $C_2H_5$ | Cl | $C_2H_5$ | H | H | |
| 2.4 | $C_2H_5$ | Cl | $CH_3$ | $CH_3$ | H | |
| 2.5 | $C_2H_5$ | Cl | $CH_3$ | H | 6-Br | |
| 2.6 | $C_2H_5$ | Cl | $CH_3$ | —$COCH_3$ | H | |
| 2.7 | $C_2H_5$ | Cl | $CH_3$ | —S—$C_6H_5$ | H | |
| 2.8 | $CF_3$ | Cl | $CH_3$ | H | H | m.p. 137–138° C. |
| 2.9 | $CH=CH_2$ | Cl | $CH_3$ | H | H | |
| 2.10 | Cyclopropyl | Cl | $CH_3$ | H | H | |
| 2.11 | $C_2H_5$ | Cl | $C_2H_5$ | H | 4-Br | |
| 2.12 | $C_2H_5$ | $NO_2$ | $CH_3$ | H | H | |
| 2.13 | $C_2H_5$ | CN | $CH_3$ | H | H | |
| 2.14 | $C_2H_5$ | Cl | Cyclopropyl | H | H | $n_D^{20} = 1.6058$ |
| 2.15 | Cl | $C_2H_5$ | $CH_3$ | H | H | |
| 2.16 | F | $C_2H_5$ | $CH_3$ | H | H | |
| 2.17 | Br | $C_2H_5$ | $CH_3$ | H | H | |
| 2.18 | $C_2H_5$ | Br | $CH_3$ | H | H | |
| 2.19 | $C_2H_5$ | F | $CH_3$ | H | H | |
| 2.20 | $C_2H_5$ | Cl | $CH_3$ | H | 4-Br | |
| 2.21 | $C_2H_5$ | Cl | $CH_3$ | H | 4-$CH_3$ | |
| 2.22 | $C_2H_5$ | Cl | $CH_3$ | H | 2-$CH_3$ | |
| 2.23 | $C_2H_5$ | Cl | $CH_3$ | H | 4-$OCH_3$ | |
| 2.24 | $C_2H_5$ | Cl | $CH_3$ | H | 4-$SCH_3$ | |
| 2.25 | $C_2H_5$ | Cl | $CH_3$ | H | 8-Cl | |
| 2.26 | $C_2H_5$ | Cl | $CH_3$ | H | 4-O—$C_6H_5$ | |
| 2.27 | $C_2H_5$ | Cl | $CH_3$ | H | 3-$OCH_3$ | |
| 2.28 | $C_2H_5$ | Cl | $CH_3$ | H | 3-Cl | |
| 2.29 | $C_2H_5$ | Cl | $CH_3$ | H | 2,3-di-$CH_3$ | |
| 2.30 | $C_2H_5$ | Cl | $CH_3$ | H | 2-OH | |
| 2.31 | $C_2H_5$ | Cl | $CH_3$ | H | 4-Cl | m.p. 77–78° C. |
| 2.32 | $C_2H_5$ | Cl | $CH_3$ | —$SCCl_3$ | H | |
| 2.33 | $C_2H_5$ | Cl | $CH_3$ | —$SCCl_2F$ | H | |
| 2.34 | $C_2H_5$ | Cl | $CH_3$ | H | 2-$OCH_3$ | m.p. 86–88° C. |

TABLE 2-continued

α-Naphthyl derivatives

| Comp No. | $R_1$ | $R_2$ | $R_4$ | $R_3$ | $R_5$ | Physical data |
|---|---|---|---|---|---|---|
| 2.35 | Cl | $NH_2$ | $CH_3$ | H | H | m.p. 175–177° C. |
| 2.36 | $C_2H_5$ | H | $CH_3$ | H | H | m.p. 114–115° C. |
| 2.37 | Cl | H | $CH_3$ | H | H | |
| 2.38 | $C_2H_5$ | $SCH_3$ | $CH_3$ | H | H | |
| 2.39 | $C_2H_5$ | $SOCH_3$ | $CH_3$ | H | H | |
| 2.40 | $C_2H_5$ | $SOCH_3$ | $CH_3$ | H | H | |
| 2.41 | Cl | $NO_2$ | $CH_3$ | H | H | m.p. 74–76° C. |
| 2.42 | $C_2H_5$ | $NH_2$ | $CH_3$ | H | H | |
| 2.43 | $C_2H_5$ | Br | $CH_3$ | H | H | m.p. 92–93° C. |
| 2.44 | $C_2H_5$ | $OCH_3$ | $CH_3$ | H | H | |
| 2.45 | $C_2H_5$ | $NHCH_3$ | $CH_3$ | H | H | |
| 2.46 | $n-C_3H_7$ | Cl | $CH_3$ | H | H | oil |
| 2.47 | $n-C_3H_7$ | $NO_2$ | $CH_3$ | H | H | |
| 2.48 | $n-C_3H_7$ | $NH_2$ | $CH_3$ | H | H | |
| 2.49 | $n-C_3H_7$ | Br | $CH_3$ | H | H | m.p. 92–94° C. |
| 2.50 | $CH_3$ | Cl | $CH_3$ | H | H | m.p. 115–116° C. |
| 2.51 | $CH_3$ | Br | $CH_3$ | H | H | m.p. 115–116° C. |
| 2.52 | $CH_3$ | $NO_2$ | $CH_3$ | H | H | |
| 2.53 | $CH_3$ | $NH_2$ | $CH_3$ | H | H | |
| 2.54 | $C_2H_5$ | Cl | $C_2H_5$ | H | 4-Cl | m.p. 108–109° C. |
| 2.55 | $C_2H_5$ | I | $CH_3$ | H | H | m.p. 82–83° C. |
| 2.56 | $CH_3$ | I | $CH_3$ | H | H | |
| 2.57 | $n-C_3H_7$ | I | $CH_3$ | H | H | |
| 2.58 | $n-C_4H_9$ | Cl | $CH_3$ | H | H | |
| 2.59 | $CH_3$ | H | $CH_3$ | H | H | m.p. 144–145° C. |
| 2.60 | $n-C_3H_7$ | H | $CH_3$ | H | H | m.p. 100–101° C. |
| 2.61 | $CH_3$ | $CH_3$ | $CH_3$ | H | H | m.p. 151–152° C. |
| 2.62 | $C_2H_5$ | $CH_3$ | $CH_3$ | H | H | |
| 2.63 | $n-C_3H_7$ | $CH_3$ | $CH_3$ | H | H | |
| 2.64 | $C_2H_5$ | $C_2H_5$ | $CH_3$ | H | H | |
| 2.65 | $CH_2OCH_3$ | Cl | $CH_3$ | H | H | |
| 2.66 | $CH_2OC_2H_5$ | Cl | $CH_3$ | H | H | |
| 2.67 | $CH_2SCH_3$ | Cl | $CH_3$ | H | H | |
| 2.68 | $CH_2SO_2CH_3$ | Cl | $CH_3$ | H | H | |
| 2.69 | $C_2H_5$ | Cl | $CH_3$ | H | $3,7-(CH_3)_2$ | m.p. 116–118° C. |
| 2.70 | $C_2H_5$ | Cl | $CH_3$ | H | 7-(—O—⟨phenyl⟩—$NO_2$) | |
| 2.71 | $C_2H_5$ | Cl | $CH_3$ | H | 7-Cl | m.p. 127–128° C. |
| 2.72 | $CH_3$ | Cl | $CH_3$ | H | 7-Cl | m.p. 130–131° C. |
| 2.73 | $CH_3$ | Cl | $C_2H_5$ | H | 7-Cl | m.p. 91–92° C. |
| 2.74 | $C_2H_5$ | Cl | $C_2H_5$ | H | 7-Cl | resin |
| 2.75 | $CF_3$ | H | $CH_3$ | H | H | resin |
| 2.76 | $CH_3$ | Cl | $CH_3$ | H | 7-Br | m.p. 140–141° C. |
| 2.77 | $C_2H_5$ | Cl | $CH_3$ | H | 7-Br | m.p. 125–127° C. |

TABLE 3

| Comp. No. | $R_1$ | $R_2$ | $R_3$ | $R_4$ C-1' | $R_8$ C-1' | $R_4$ C-2' | $R_8$ C-2' | $R_5$ | Physical data |
|---|---|---|---|---|---|---|---|---|---|
| 3.1 | $C_2H_5$ | Cl | H | H | H | H | H | H | m.p. 84–86° C. |
| 3.2 | $C_2H_5$ | Cl | H | $CH_3$ | H | H | H | H | m.p. 76-78° C. |
| 3.3 | $C_2H_5$ | Cl | H | $C_2H_5$ | H | H | H | H | oil |
| 3.4 | $C_2H_5$ | Cl | H | n-Propyl | H | H | H | H | |
| 3.5 | $C_2H_5$ | Cl | H | i-Propyl | H | H | H | H | |
| 3.6 | $C_2H_5$ | Cl | H | $CH_3$ | H | $CH_3$ | H | H | |
| 3.7 | $C_2H_5$ | Cl | H | $CH_3$ | H | $C_2H_5$ | H | H | |
| 3.8 | $C_2H_5$ | Cl | H | H | H | $CH_3$ | $CH_3$ | H | m.p. 92–94° C. |
| 3.9 | $C_2H_5$ | Cl | H | $CH_3$ | H | $CH_3$ | $CH_3$ | H | |
| 3.10 | $C_2H_5$ | Cl | H | H | H | $CH_3$ | H | H | |
| 3.11 | $C_2H_5$ | Cl | H | H | H | i-Propyl | H | H | |
| 3.12 | $CH_3$ | Cl | H | H | H | H | H | H | |
| 3.13 | $CH_3$ | Cl | H | $CH_3$ | H | H | H | H | |
| 3.14 | $C_2H_5$ | Cl | H | $CH_3$ | $CH_3$ | H | H | H | |
| 3.15 | $C_2H_5$ | Cl | H | $CH_3$ | H | H | H | 6-$CH_3$ |  |
| 3.16 | $C_2H_5$ | Cl | H | $CH_3$ | H | $CH_3$ | $CH_3$ | 6-$CH_3$ | |
| 3.17 | $C_2H_5$ | Cl | H | $CH_3$ | H | H | H | 6-$OCH_3$ | |
| 3.18 | $C_2H_5$ | Cl | H | $CH_3$ | H | $CH_3$ | $CH_3$ | 6-$OCH_3$ | |
| 3.19 | $C_2H_5$ | Cl | H | $CH_3$ | H | H | H | 6-$OCHF_2$ | |
| 3.20 | $C_2H_5$ | $NO_2$ | H | $CH_3$ | H | H | H | H | |
| 3.21 | $C_2H_5$ | $SCH_3$ | H | $CH_3$ | H | H | H | H | |
| 3.22 | $C_2H_5$ | $SOCH_3$ | H | $CH_3$ | H | H | H | H | |
| 3.23 | $C_2H_5$ | $SO_2CH_3$ | H | $CH_3$ | H | H | H | H | |
| 3.24 | $CH_3$ | Cl | H | H | H | H | H | H | |
| 3.25 | $CF_3$ | Cl | H | H | H | H | H | H | |
| 3.26 | $CF_3$ | Cl | H | —$CH_3$ | H | H | H | H | |
| 3.27 | $CH_3$ | Cl | H | —$CH_3$ | H | H | H | H | m.p. 90–91° C. |
| 3.28 | $CH_3$ | Br | H | —$CH_3$ | H | H | H | H | |
| 3.29 | $CH_3$ | $NO_2$ | H | —$CH_3$ | H | H | H | H | |
| 3.30 | $C_2H_5$ | Br | H | —$CH_3$ | H | H | H | H | |
| 3.31 | $C_2H_5$ | $NO_2$ | H | —$CH_3$ | H | H | H | H | |
| 3.32 | $C_2H_5$ | $SCH_3$ | H | —$CH_3$ | H | H | H | H | |
| 3.33 | $CH_3$ | Cl | H | H | H | $CH_3$ | $CH_3$ | H | m.p. 130–131° C. |

TABLE 4

| Comp. No. | $R_1$ | $R_2$ | $R_3$ | $R_4$ C-1' | $R_8$ C-1' | $R_4$ C-2' | $R_8$ C-2' | $R_5$ | Physical data |
|---|---|---|---|---|---|---|---|---|---|
| 4.1 | $C_2H_5$ | Cl | H | H | H | H | H | H | m.p. 94–96° C. |
| 4.2 | $C_2H_5$ | Cl | H | $CH_3$ | H | H | H | H | |
| 4.3 | $C_2H_5$ | Cl | H | $CH_3$ | H | $CH_3$ | $CH_3$ | H | |
| 4.4 | $C_2H_5$ | Cl | H | $C_2H_5$ | H | H | H | H | |
| 4.5 | $C_2H_5$ | Cl | H | $CH_3$ | H | $CH_3$ | $CH_3$ | H | |
| 4.6 | $C_2H_5$ | Cl | H | H | H | $CH_3$ | H | H | |
| 4.7 | $C_2H_5$ | Cl | H | H | H | $CH_3$ | $CH_3$ | H | |
| 4.8 | $C_2H_5$ | Cl | H | H | H | i-Propyl | H | H | |
| 4.9 | $CH_3$ | Cl | H | H | H | H | H | H | |
| 4.10 | $CH_3$ | Cl | H | $CH_3$ | H | H | H | H | |
| 4.11 | $CH_3$ | Cl | H | H | H | $CH_3$ | $CH_3$ | H | m.p. 81–82° C. |

TABLE 5

Structure: pyrimidine-N(R₃)-C1'(R₄,R₈)-C2'(R₄,R₈)-C3'(R₄,R₈)-naphthyl(R₅), with R₁ and R₂ on pyrimidine ring.

| Comp. No. | R₁ | R₂ | R₃ | R₄ C-1' | R₈ C-1' | R₄ C-2' | R₈ C-2' | R₄ C-3' | R₈ C-3' | R₅ | Physical data |
|---|---|---|---|---|---|---|---|---|---|---|---|
| 5.1 | C₂H₅ | Cl | H | H | H | H | H | H | H | H | oil |
| 5.2 | C₂H₅ | Cl | H | CH₃ | H | H | H | H | H | H | |
| 5.3 | C₂H₅ | Cl | H | C₂H₅ | H | H | H | H | H | H | |
| 5.4 | C₂H₅ | Cl | H | CH₃ | H | H | H | CH₃ | H | H | |
| 5.5 | CH₃ | Cl | H | CH₃ | H | H | H | H | H | H | |
| 5.6 | C₂H₅ | Cl | H | H | H | H | H | H | H | 1-OCH₃ | m.p. 91–92° C. |

TABLE 6

Structure: pyrimidine with R$_1$, R$_2$, R$_3$, R$_{13}$ substituents

| Comp. No. | R$_1$ | R$_2$ | R$_3$ | R$_{13}$ | Physical data |
|---|---|---|---|---|---|
| 6.1 | n-C$_3$H$_7$ | Br | OH | H | m.p. 175–176° C. |
| 6.2 | n-C$_3$H$_7$ | Br | Cl | H | oil |
| 6.3 | (CH$_3$)$_2$CH | Br | OH | H | |
| 6.4 | (CH$_3$)$_2$CH | Br | Cl | H | |
| 6.5 | n-C$_3$H$_7$ | H | Cl | H | oil |
| 6.6 | n-C$_4$H$_9$ | Cl | Cl | H | |
| 6.7 | (CH$_3$)$_2$CH | Cl | Cl | H | |
| 6.8 | (CH$_3$)$_2$CH | Cl | OH | H | |
| 6.9 | (CH$_3$)$_2$CH | I | Cl | H | |
| 6.10 | C$_2$H$_5$ | Br | OH | H | m.p. 175–176° C. |
| 6.11 | C$_2$H$_5$ | Br | Cl | H | b.p. 112–114° C./2400 Pa |
| 6.12 | C$_2$H$_5$ | F | Cl | H | |
| 6.13 | n-C$_3$H$_7$ | I | Cl | H | oil |
| 6.14 | n-C$_3$H$_7$ | F | Cl | H | |
| 6.15 | n-C$_3$H$_7$ | Cl | Cl | H | b.p. 92–95° C./1100 Pa |
| 6.16 | C$_2$H$_5$ | I | OH | H | m.p. 191–192° C. |
| 6.17 | C$_2$H$_5$ | I | Cl | H | m.p. 56–57° C. |
| 6.18 | n-C$_4$H$_9$ | NO$_2$ | OH | H | |
| 6.19 | n-C$_3$H$_7$ | NO$_2$ | OH | H | |
| 6.20 | C$_2$H$_5$ | NO$_2$ | OH | H | m.p. 181–183° C. |
| 6.21 | (CH$_3$)$_2$CH | NO$_2$ | OH | H | |
| 6.22 | (CH$_3$)$_2$CH | NO$_2$ | Cl | H | |
| 6.23 | C$_2$H$_5$ | NO$_2$ | Cl | H | oil |
| 6.24 | C$_2$H$_5$ | NH$_2$ | Cl | H | |
| 6.25 | n-C$_3$H$_7$ | NH$_2$ | Cl | H | |
| 6.26 | n-C$_4$H$_9$ | NO$_2$ | Cl | H | |
| 6.27 | CF$_3$ | Cl | Cl | H | b.p. 50° C./1600 Pa |
| 6.28 | CF$_3$ | Br | Cl | H | |
| 6.29 | n-C$_3$H$_7$ | NO$_2$ | Cl | H | |
| 6.30 | n-C$_3$H$_7$ | NH$_2$ | Cl | H | |
| 6.31 | (CH$_3$)$_2$CH | H | Cl | H | |
| 6.32 | n-C$_4$H$_9$ | H | Cl | H | |
| 6.33 | n-C$_4$H$_9$ | Cl | Cl | H | |
| 6.34 | —C$_4$H$_9$ | Br | Cl | H | |
| 6.35 | C$_2$H$_5$ | Br | OH | CH$_3$ | m.p. 179–180° C. |
| 6.36 | C$_2$H$_5$ | Br | Cl | CH$_3$ | oil |
| 6.37 | C$_2$H$_5$ | Cl | Cl | CH$_3$ | oil |
| 6.38 | n-C$_3$H$_7$ | Cl | OH | CH$_3$ | |
| 6.39 | n-C$_3$H$_7$ | Cl | Cl | CH$_3$ | |
| 6.40 | n-C$_3$H$_7$ | Cl | OH | CH$_3$ | |
| 6.41 | n-C$_3$H$_7$ | Cl | Cl | CH$_3$ | |
| 6.42 | n-C$_3$H$_7$ | Br | OH | CH$_3$ | |
| 6.43 | n-C$_3$H$_7$ | Br | Cl | CH$_3$ | |
| 6.44 | n-C$_3$H$_7$ | I | OH | CH$_3$ | |
| 6.45 | n-C$_3$H$_7$ | I | Cl | CH$_3$ | |
| 6.46 | n-C$_3$H$_7$ | I | OH | H | m.p. 181–183° C. |
| 6.47 | —CH(CH$_3$)C$_2$H$_5$ | Cl | Cl | H | oil |
| 6.48 | —CH(CH$_3$)CH$_2$—CH=CH$_2$ | Cl | Cl | H | oil |
| 6.49 | —CH(CH$_3$)CH$_2$—C≡CH | Cl | Cl | H | |
| 6.50 | —CHCl—CH$_3$ | Cl | Cl | H | oil |
| 6.51 | —CH(CH$_3$)—SCH$_3$ | Cl | Cl | H | oil |
| 6.52 | —CH(CH$_3$)—SOCH$_3$ | Cl | Cl | H | oil |
| 6.53 | —CH(CH$_3$)—SO$_2$CH$_3$ | Cl | Cl | H | m.p. 94–95° C. |

TABLE 7

β-Naphthyl derivatives

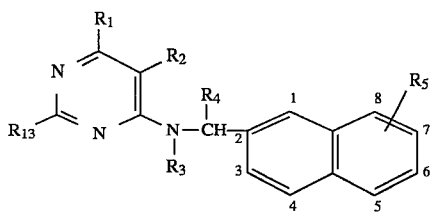

| Comp. No. | $R_1$ | $R_2$ | $R_{13}$ | $R_4$ | $R_3$ | $R_5$ | Physical data |
|---|---|---|---|---|---|---|---|
| 7.1 | Cl | $CH_3$ | $C_2H_5$ | $CH_3$ | H | H | m.p. 83–84° C. |
| 7.2 | F | $C_2H_5$ | $C_2H_5$ | $CH_3$ | H | H | oil |
| 7.3 | $CH_3$ | Cl | $CH_3$ | $CH_3$ | H | H | |
| 7.4 | $CH_3$ | Br | $CH_3$ | $CH_3$ | H | H | |
| 7.5 | Cl | $NH_2$ | $(CH_3)_2CH$ | $CH_3$ | H | H | m.p. 128–129° C. |
| 7.6 | $CH_3$ | I | $CH_3$ | $CH_3$ | H | H | |
| 7.7 | n-$C_3H_7$ | H | $CH_3$ | $CH_3$ | H | H | |
| 7.8 | Cl | $NH_2$ | $CH_3$ | $CH_3$ | H | H | resin |
| 7.9 | $CH_3$ | Cl | $CH_3$ | $CH_3$ | H | 6-Br | |
| 7.10 | $CH_3$ | Cl | $CH_3$ | $C_2H_5$ | H | 6-$OCH_3$ | |
| 7.11 | n-$C_3H_7$ | Cl | $CH_3$ | $CH_3$ | H | H | |
| 7.12 | $C_2H_5$ | Br | $CH_3$ | $CH_3$ | H | H | oil |
| 7.13 | Cyclopropyl | Cl | $CH_3$ | $CH_3$ | H | H | |
| 7.14 | $CH_3$ | H | $(CH_3)_2CH$ | $CH_3$ | H | H | oil |
| 7.15 | $CH_3$ | Cl | $(CH_3)_2CH$ | $CH_3$ | H | H | oil |
| 7.16 | $CH(CH_3)_2$ | H | $CH_3$ | $CH_3$ | H | H | |
| 7.17 | Cl | Cl | Cl | $CH_3$ | H | H | |
| 7.18 | $C_2H_5$ | Cl | $CH_3$ | $CH_3$ | H | H | oil |
| 7.19 | H | Cl | Cl | $CH_3$ | H | H | |
| 7.20 | n-$C_3H_5$ | Br | $CH_3$ | $CH_3$ | H | H | |
| 7.21 | Cl | Br | Cl | $CH_3$ | H | H | |
| 7.22 | $C_2H_5$ | H | $CH_3$ | $CH_3$ | H | H | oil |
| 7.23 | H | F | $SCH_3$ | $CH_3$ | H | H | |
| 7.24 | $C_2H_5$ | Cl | n-$C_4H_9$ | $CH_3$ | H | H | |
| 7.25 | H | $CH_3$ | Cl | $CH_3$ | H | H | m.p. 143–144° C. |
| 7.26 | $C_2H_5$ | Cl | $N(CH_3)_2$ | $CH_3$ | H | H | |
| 7.27 | n-$C_3H_7$ | I | $CH_3$ | $CH_3$ | H | H | |
| 7.28 | $CH(CH_3)_2$ | Cl | $CH_3$ | $CH_3$ | H | H | |
| 7.29 | Cl | Cl | $N(CH_3)_2$ | $CH_3$ | H | H | |
| 7.30 | $C_2H_5$ | Cl | $N(CH_3)_2$ | $CH_3$ | H | H | |
| 7.31 | H | $CH_3$ | $OCH_3$ | $CH_3$ | H | H | m.p. 127–128° C. |
| 7.32 | H | $CH_3$ | $SCH_3$ | $CH_3$ | H | H | resin |
| 7.33 | n-$C_3H_7$ | Cl | Cl | $CH_3$ | H | H | |
| 7.34 | n-$C_3H_7$ | Cl | $OCH_3$ | $CH_3$ | H | H | |
| 7.35 | $CH_3$ | H | $CH_3$ | $CH_3$ | H | H | resin |
| 7.36 | $CH(CH_3)_2$ | Cl | Cl | $CH_3$ | H | H | |
| 7.37 | $CH(CH_3)_2$ | Cl | $OCH_3$ | $CH_3$ | H | H | |
| 7.38 | H | I | Cl | $CH_3$ | H | H | |
| 7.39 | $C_2H_5$ | Cl | $CH_3$ | $CH_3$ | H | 6-Br | oil |
| 7.40 | Cl | Br | $N(CH_3)_2$ | $CH_3$ | H | H | |
| 7.41 | $C_2H_5$ | I | $CH_3$ | $CH_3$ | H | 6-$CH_3$ | |
| 7.42 | $C_2H_5$ | Br | $CH_3$ | $CH_3$ | H | 6-Br | m.p. 103–104° C. |
| 7.43 | H | F | $OC_2H_5$ | $CH_3$ | H | H | |
| 7.44 | $C_2H_5$ | Br | Cl | $CH_3$ | H | H | |
| 7.45 | $C_2H_5$ | F | $CH_3$ | $CH_3$ | H | H | |
| 7.46 | $C_2H_5$ | Br | $CH_3$ | $CH_3$ | H | 6-$CH_3$ | oil |
| 7.47 | $C_2H_5$ | Cl | $CH_3$ | $CH_3$ | H | 6-$CH_3$ | oil |
| 7.48 | $CH(CH_3)_2$ | Br | $CH_3$ | $CH_3$ | H | H | |
| 7.49 | Cl | I | $CH_3$ | $CH_3$ | H | H | |
| 7.50 | H | Cl | $OCH_3$ | $CH_3$ | H | H | |
| 7.51 | $C_2H_5$ | Cl | Cl | $CH_3$ | H | H | |
| 7.52 | $C_2H_5$ | Cl | $C_2H_5$ | $CH_3$ | H | H | |
| 7.53 | $CH(CH_3)C_2H_5$ | Cl | $CH_3$ | $CH_3$ | H | H | |
| 7.54 | $C_2H_5$ | Cl | $SCH_3$ | $CH_3$ | H | H | |
| 7.55 | n-$C_4H_9$ | Cl | $CH_3$ | $CH_3$ | H | H | |
| 7.56 | n-$C_4H_9$ | Br | $CH_3$ | $CH_3$ | H | H | |
| 7.57 | H | Cl | $SCH_3$ | $CH_3$ | H | H | |
| 7.58 | H | F | Cl | $CH_3$ | H | H | |
| 7.59 | $C_2H_5$ | I | $CH_3$ | $CH_3$ | H | H | |
| 7.60 | $C_2H_5$ | I | Cl | $CH_3$ | H | H | |
| 7.61 | $C_2H_5$ | Cl | Cyclopropyl | $CH_3$ | H | H | |
| 7.62 | $C_2H_5$ | Br | $OC_2H_5$ | $CH_3$ | H | H | |
| 7.63 | $C_2H_5$ | Cl | $CH(CH_3)_2$ | $CH_3$ | H | H | |

TABLE 7-continued

β-Naphthyl derivatives

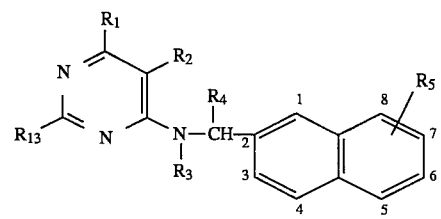

| Comp. No. | R₁ | R₂ | R₁₃ | R₄ | R₃ | R₅ | Physical data |
|---|---|---|---|---|---|---|---|
| 7.64 | C₂H₅ | Cl | OCH₃ | CH₃ | H | H | |
| 7.65 | C₂H₅ | Br | C₂H₅ | CH₃ | H | H | |
| 7.66 | C₂H₅ | Cl | C₂H₅ | CH₃ | H | 6-Br | |
| 7.67 | C₂H₅ | Cl | n-C₃H₇ | CH₃ | H | H | |
| 7.68 | C₂H₅ | Cl | CH₃ | Cyclopropyl | H | H | |
| 7.69 | C₂H₅ | Br | SC₂H₅ | CH₃ | H | H | |
| 7.70 | C₂H₅ | Cl | Cyclopropyl | C₂H₅ | H | H | |
| 7.71 | C₂H₅ | Br | n-C₃H₇ | CH₃ | H | H | |
| 7.72 | C₂H₅ | Br | CH(CH₃)₂ | CH₃ | H | H | |
| 7.73 | Cyclopropyl | Cl | CH₃ | CH₃ | H | H | |
| 7.74 | Cyclopropyl | Cl | CH₃ | CH₃ | H | 6-Br | |
| 7.75 | C₂H₅ | Br | Cyclopropyl | CH₃ | H | H | |
| 7.76 | C₂H₅ | Cl | CF₃ | CH₃ | H | H | |
| 7.77 | C₂H₅ | Cl | CCl₃ | CH₃ | H | H | |
| 7.78 | Cl | H | CCl₃ | CH₃ | H | H | |
| 7.79 | Cl | Cl | CCl₃ | CH₃ | H | H | |
| 7.80 | Cl | Br | CCl₃ | CH₃ | H | H | |
| 7.81 | C₂H₅ | Cl | CH₂OCH₃ | CH₃ | H | H | |
| 7.82 | C₂H₅ | Br | CH₂OCH₃ | CH₃ | H | H | |
| 7.83 | Cl | Cl | CH₂OCH₃ | CH₃ | H | H | |

TABLE 8

α-Naphthyl derivatives

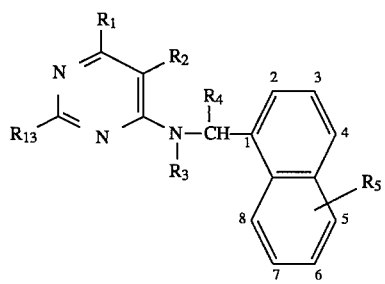

| Comp. No. | R₁ | R₂ | R₁₃ | R₄ | R₃ | R₅ | Physical data |
|---|---|---|---|---|---|---|---|
| 8.1 | C₂H₅ | Br | CH | CH₃ | H | H | oil |
| 8.2 | H | Cl | Cl | CH₃ | H | H | |
| 8.3 | C₂H₅ | Cl | CH₃ | CH₃ | H | H | m.p. 104–105° C. |
| 8.4 | n-C₃H₇ | Br | CH₃ | CH₃ | H | H | |
| 8.5 | CH₃ | Cl | CH₃ | CH₃ | H | H | |
| 8.6 | H | F | Cl | CH₃ | H | H | |
| 8.7 | C₂H₅ | Cl | CH₃ | C₂H₅ | H | H | |
| 8.8 | CH₃ | Cl | (CH₃)₂CH | CH₃ | H | H | oil |
| 8.9 | n-C₃H₇ | Cl | CH₃ | CH₃ | H | H | |
| 8.10 | H | Cl | OCH₃ | CH₃ | H | H | |
| 8.11 | CH₃ | Cl | CH₃ | CH₃ | H | H | |
| 8.12 | CH₃ | Cl | CH₃ | C₂H₅ | H | H | |
| 8.13 | C₂H₅ | H | CH₃ | CH₃ | H | H | oil |
| 8.14 | H | I | Cl | CH₃ | H | H | |
| 8.15 | Cl | I | Cl | CH₃ | H | H | |
| 8.16 | n-C₃H₇ | I | CH₃ | CH₃ | H | H | |
| 8.17 | C₂H₅ | I | CH₃ | CH₃ | H | H | |

TABLE 8-continued

α-Naphthyl derivatives

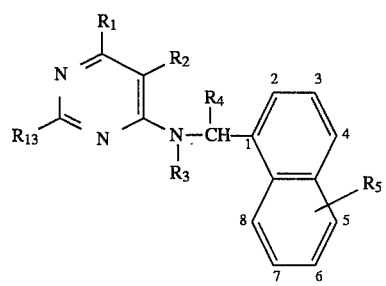

| Comp. No. | R₁ | R₂ | R₁₃ | R₄ | R₃ | R₅ | Physical data |
|---|---|---|---|---|---|---|---|
| 8.18 | C₂H₅ | Cl | Cl | CH₃ | H | H | |
| 8.19 | Cl | Br | Cl | CH₃ | H | H | |
| 8.20 | Cl | Cl | N(CH₃)₂ | CH₃ | H | H | |
| 8.21 | C₂H₅ | Cl | N(CH₃)₂ | CH₃ | H | H | |
| 8.22 | n-C₃H₇ | Cl | Cl | CH₃ | H | H | |
| 8.23 | C₂H₅ | Br | Cl | CH₃ | H | H | |
| 8.24 | H | F | OCH₃ | CH₃ | H | H | |
| 8.25 | CH₃ | Br | CH₃ | CH₃ | H | H | |
| 8.26 | C₂H₅ | I | Cl | CH₃ | H | H | |
| 8.27 | C₂H₅ | Cl | C₂H₅ | CH₃ | H | H | |
| 8.28 | CH₃ | I | CH₃ | CH₃ | H | H | |
| 8.29 | Cl | Cl | Cl | CH₃ | H | H | |
| 8.30 | H | Cl | SCH₃ | CH₃ | H | H | |
| 8.31 | n-C₄H₉ | Cl | CH₃ | CH₃ | H | H | |

NMR data of non-crystallising compounds

| Comp. No. | NMR; ppm values |
|---|---|
| 1.18 | 8.2 S (pyrim.); 7.5–7.9 M (arom. H); 5.6 M (CHN); 5.1 D (NH); 2.5 Q (CH$_2$); 1.7 D (CH$_3$); 1.1 T (CH$_3$). |
| 1.43 | 8.3 S (pyrim.); 7.2–8.2 M (arom. H); 5.8 M (CH—N, NH); 4.1 S (OCH$_3$); 2.7 Q (—CH$_2$—); 1.6 D (—CH$_3$); 1.2 T (—CH$_3$). |
| 1.45 | 8.4 S (pyrim.); 7.0–7.8 M (arom. H); 5.7 D (NH); 5.3 m (CH—N); 4.1 s (OCH$_3$); 2.7 Q (—CH$_2$—); 1.7 M (—CH$_2$); 1.1 M (—CH$_3$, n CH$_3$). |
| 1.48 | 8.3 S (pyrim.); 7.3–8.3 M (arom. H); 7.2 D (J = 70 Hz), (F—CH); 6.9 D (J = 70 Hz), (F—CH); 5.8 D (—N—H); 5.7 M (CH—N); 2.8 M (—CH$_2$—); 1.6 D (CH$_3$); 1.2 T (—CH$_3$). |
| 1.53 | 8.2 S (pyrim.); 7.2–7.9 M (arom. H); 5.2–5.8 M (CH and NH); 2.4 S (CH$_3$); 1.2 D (CH$_3$). |
| 1.55 | 8.3 S (pyrim.); 7.0–7.7 M (arom. H); 5.68 D (NH); 5.24 Q (C—H); 3.86 S (—OCH$_3$), 2.42 S (—CH$_3$), 2.0 M (—CH$_2$—), 0.96 T (—CH$_3$). |
| 1.56 | 8.34 S (pyrim.); 7.2–7.4 M (arom. H); 5.66 D (N—H), 5.46 M (CHN); 2.46 S (—CH$_3$), 2.42 S (—CH$_3$), 1.64 D (—CH$_3$) |
| 1.58 | 8.3 S (pyrim.); 7.3–8.1 M (arom. H); 6.0 D (—NH), 5.8 M (—C—H); 4.1 (OCH$_3$), 2.44 S (—CH$_3$), 1.6 D (—CH$_3$). |
| 1.61 | 8.5 S (pyrim.); 7.2–7.9 M (arom. H); 6.6 D (NH); 5.5 M (CHN); 2.8 Q (CH$_2$); 2.2 S (SCH$_3$); 1.7 D (CH$_3$); 1.2 T (CH$_3$). |
| 1.80 | 8.4 S (pyrim.); 8.0 D (NH); 7.2–7.8 M (arom. H); 5.6 M (CHN); 2.7 Q (CH$_2$); 1.7 D (CH$_3$); 1.3 T (CH$_3$). |
| 1.84 | 8.4 S (pyrim.); 7.2–7.8 M (arom. H); 5.2–5.8 (CH and NH); 2.5–2.9 Q (CH$_2$); 1.6 D (CH$_3$); 1.2 T (CH$_3$). |
| 1.86 | 8.4 S (pyrim.); 7.2–7.8 M (arom. H); 5.2–5.7 M (CHN, NH); 2.75 (CH$_2$); 1.3–1.9 D+M (CH$_3$CH, CH$_2$); 1.0 T (CH$_3$). |
| 1.89 | 8.4 S (pyrim.); 7.3–8.0 M (arom. H); 5.3 M (NH and CH); 2.6–2.9 T (CH$_2$); 1.4–2.1 M (CH$_2$ and CH$_3$); 1.0 T (CH$_3$). |
| 1.100 | 8.3 S (pyrim.); 7.2–7.9 M (arom. H); 5.7 (NH); 5.4 Q (CH); 2.7 Q (CH$_2$); 1.6 D (CH$_3$); 1.2 T (CH$_3$). |
| 1.108 | 8.4 S (pyrim.); 7.3–7.9 M (arom. H); 8.3–8.8 broad (NH); 5.5 M (CH); 2.4–3.1 Q (CH$_2$) + Q (CH$_2$S); 1.7 D (CH$_3$); 1.2 (2 × CH$_3$). |
| 1.148 | 8.2 S (pyrim.); 7.3–8.2 M (arom. H); 7.22 D (CHF); 6.92 D (CHF), 5.78 Δ (N—H), 5.66 M (—CH), 2.44 S (CH$_3$); 1.6 D (—CH$_3$). |
| 1.150 | 8.4 S (pyrim.); 7.4–8.0 M (arom. H); 5.3–5.9 M (NH, CH); 2.8 Q (CH$_2$); 1.7 D (CH$_3$); 1.3 T (CH$_3$). |
| 1.151 | 8.3 S (pyrim.); 7.2–7.8 M (arom. H); 5.3–5.9 M (NH, CH); 2.8 Q (CH$_2$); 2.5 S (CH$_3$); 1.6 D (CH$_3$); 1.3 T (CH$_3$). |
| 2.46 | 8.4 S (pyrim.); 7.1–8.1 M (arom. H); 6.1 P (CH); 5.6 D (NH); 2.7 T (CH$_2$); 1.4–1.9 M (CH$_2$); 1.7 D (CH$_3$); 1.0 T (CH$_3$). |
| 2.74 | 8.38 S (pyrim.); 7.34–8.26 M (arom. H); 5.9 Q (—CH); 5.66 D (N—H); 2.78 Q (—CH$_2$), 2.06 M (CH$_2$) 1.24 T (—CH$_3$), 1.02 T (—CH$_3$). |
| 3.3 | 8.3 S (pyrim.); 7.1–7.8 M (arom. H); 5.2 D (N—H); 4.6 M (CH); 2.4–3.0 M (CH$_2$); 0.8–1.7 M (CH$_2$, CH$_3$). |
| 6.2 | 8.8 S (pyrim.); 3.0 T (CH$_2$); 1.8 M (CH$_2$); 1.05 T (CH$_3$). |
| 6.5 | 8.9 S (pyrim.); 7.3 S (pyrim.); 2.7 (CH$_2$); 1.4–2.1 M (CH$_2$); 1.0 T (CH$_3$). |
| 6.23 | 9.0 S (pyrim.); 2.8 Q (CH$_2$); 1.35 T (CH$_3$). |
| 7.47 | 7.2–7.8 M (arom. H; 5.3–5.7 (CH, NH); 2.5–2.9 Q (CH$_2$); 2.55 (CH$_3$); 2.6–2.7 D (CH$_3$); 1.2 T (CH$_3$). |
| 8.1 | 7.2–8.3 M (arom. H); 6.0–6.4 M; 5.5–5.8 D (NH); 2.6–3.0 Q (CH$_2$); 2.5 S (CH$_3$); 2.7 D (CH$_3$); 2.2 T (CH$_3$); |
| 8.8 | 7.2–8.3 M (arom. H); 6.0–6.4 M (CH); 5.3–5.6 D (NH); 2.5–3.1 M (CH); 2.4 S (CH$_3$); 1.7 D (CH$_3$); 1.1 T (CH$_3$). |
| 8.13 | 7.3–8.3 M (arom. H); 5.8 S (pyrim.); 5.3–5.8 M (CH, NH); 2.55 (CH$_3$); 2.3–2.6 Q (CH$_2$); 2.7 D (CH$_3$); 1.3–2.0 M (CH); 1.1 T (CH$_3$). |
| 1.101 | 8.2 S (pyrim.); 7.2–7.9 M (arom. H); 5.2–5.9 M (NH, CH); 2.6 S (CH$_3$); 1.6 D (CH$_3$). |
| 1.161 | 8.4 S (pyrim.); 7.1–7.9 M (arom. H); 5.2–5.9 M (NH, CH); 4.5 S (OCH$_2$); 3.55 (OCH$_3$); 2.7 D (CH$_3$). |
| 1.70 | 8.3 S (pyrim.); 7.1–7.7 (arom.), 5.9 D (NH); 4.9 M (CHN); 3.9 S (OCH$_3$); 2.8 Q (CH$_2$); 1.3 T (CH$_3$); 0.5–0.7 (M) (cycl.). |
| 1.74 | 7.4–8.4M(arom. H and pyrim-H); 5.73d(—NH); 5.43Q(—CH—); 2.8Q(—CH$_2$); 1.97M(—CH$_2$—); 1.43M(—CH$_2$—); 1.26M(CH$_3$); 1.0T(CH$_3$). |

-continued

NMR data of non-crystallising compounds

| Comp. No. | NMR; ppm values |
|---|---|
| 1.88 | 7.4–8.45M(arom. H and pyrim-H); 5.37Q(—CH—); 2.45S(CH$_3$); 2.0M(—CH$_2$—); 1.45M(—CH$_2$—); 1.0T(CH$_3$). |
| 3.30 | 7.35–8.45 M (arom. H and pyrim-H); 5.38 D (NH); 4.6 m (CH$_2$); 3.13 M (CH$_2$); 2.95 M (—CH$_2$); 2.28 M (CH$_2$); 1.26 M (CH$_3$). |
| 5.1 | 7.3–8.5 M (arom. H and pyrim-H); 5.36 S broad (NH); 3.58 Q (CH$_2$); 2.9 M (CH$_2$); 2.75 M (CH$_2$); 2.10 (CH$_2$); 1.25 T (CH$_3$). |
| 1.154 | 8.3 S (pyrim.); 7.0–7.8 M (arom. H); 5.6–5.9 D (NH); 5.1–5.4 Q (NCH); 3.95 (OCH$_3$); 2.6–3.0 Q (CH$_2$); 1.4–2.3 M (CH$_2$); 0.8–1.4 M (2 × CH$_3$). |
| 1.155 | 8.35 S (pyrim); 7.2–7.8 M (arom. H); 5.2–5.9 M (NH; CH); 2.6–3.0 Q (CH2); 2.5 S (CH$_3$); 2.4–2.6 D (CH$_3$); 1.1–1.4 T (CH$_3$). |
| 1.181 | 8.4 S (pyrim.); 7.1–7.9 M (arom. H); 6.4–6.9 D (NH); 5.2–5.6 Q (CHN); 2.6–3.0 Q (CH$_2$); 0.8–2.3 M (aliph. H). |
| 1.182 | 8.3 S (pyrim.); 7.2–7.9 M (arom. H); 5.3–5.9 M (NH; CHN); 2.6–3.0 Q (CH$_2$); 1.6–1.8 D (CH$_3$); 1.1–1.4 T (CH$_3$). |
| 2.75 | 8.6 S (pyrim.); 7.3–8.2 M (arom. H); 6.5 S (pyrim.); 5.8 broad (NH); 1.7–1.8 D CH$_3$). |
| 7.2 | 7.3–8.0 M (arom. H); 5.4–5.8 M (CHN); 4.8–5.2 D (NH); 2.2–2.9 M (2×CH$_2$); 2.6–2.8 D (CH$_3$); 0.9–1.4 M (2×CH$_3$). |
| 7.8 | 7.2–7.9 M (arom. H); 5.2–5.6 M (NH, CHN); 3.0–3.6 broad (NH); 2.4 S (CH$_3$); 1.5–1.7 D (CH$_3$). |
| 7.12 | 7.3–8.0 M (arom. H); 5.6–5.9 M (CH, NH); 2.6–3.9 Q (CH$_2$); 2.4 S (CH$_3$); 1.6–1.8 D (CH$_3$); 1.2 T (CH$_3$). |
| 7.14 | 7.3–7.9 M (arom. H); 5.9 S (pyrim.); 5.3–5.7 broad (NH); 4.7–5.1 M (CH); 2.5–3.7 M (CH); 2.2 S (CH$_3$); 1.5–1.7 D (CH$_3$); 1.2–1.4 D (CH$_3$). |
| 7.15 | 7.2–7.9 M (arom. H); 5.3–5.7 M (CH, NH); 2.5–3.2 M (CH); 2.4 S (CH$_3$); 2.6–2.8 D (CH$_3$); 1.2 T (CH$_3$). |
| 7.18 | 7.3–8.9 M (arom. H); 5.3–5.7 M (NH, CH); 2.5–2.9 Q (CH$_2$); 2.45 (CH$_3$); 2.6 D (CH$_3$); 1.1 T (CH$_3$). |
| 7.22 | 7.3–7.9 M (arom. H); 5.8 S (pyrim.); 5.3–5.5 D (NH); 5.0 M (CH); 2.3–2.7 Q (CH$_2$); 2.5 S (CH$_3$); 1.6 D (CH$_3$); 1.2 T (CH$_3$); |
| 7.32 | 7.3–7.9 M (arom. H); 5.3–5.7 Q (CH); 4.6–5.0 broad (NH); 2.3 S (SCH$_3$); 1.9 S (CH$_3$); 1.6 D (CH$_3$). |
| 7.35 | 7.2–7.9 M (arom. H); 5.8 S (pyrim.); 5.2–5.5 M (NH); 4.6–5.0 M (CH); 2.5 S (CH$_3$); 2.2 S (CH$_3$); 1.5 D (CH$_3$). |
| 7.39 | 7.3–7.9 M (arom. H); 5.2–5.7 M (CH, NH); 2.5–2.9 Q (CH$_2$); 2.4 S (CH$_3$); 1.5–1.7 D (CH$_3$); 1.2 T (CH$_3$); |
| 7.46 | 7.2–7.9 M (arom. H); 5.3–5.8 M (CH, NH); 2.4–3.0 Q (CH$_2$); 2.5 S (2×CH$_2$); 2.6–2.7 D (CH$_3$); 1.2 T (CH$_3$). |
| 6.2 | 8.9 S (pyrim.); 3.0 T (CH$_2$); 1.5–2.1 M (CH$_2$); 1.0 T (CH$_3$); |
| 6.5 | 8.9 S (pyrim.); 7.2 S (pyrim.); 2.8 T (CH$_2$); 1.4–2.0 M (CH$_2$); 0.1 T (CH$_3$). |
| 6.13 | 8.7 S (pryim.); 3.0 T (CH$_2$); 1.4–2.1 M (CH$_2$); 1.0 T (CH$_3$). |
| 6.36 | 2.9 Q (CH$_2$); 2.7 S (CH$_3$); 1.3 T (CH$_3$). |
| 6.37 | 2.9 Q (CH$_2$); 2.7 S (CH$_3$); 1.3 T (CH$_3$). |
| 6.47 | 8.80 (s, 1H, pyrimidine); 3.42–3.35 (m, 1H, CH); 1.87–1.79 (m, 1H, CH); 1.67–1.58 (m, 1H, CH); 1.25 (d, 3H, CH$_3$); 0.87 (t, 3H, CH$_3$). |
| 6.48 | 8.78 (s, 1H, pyrimidine); 5.77–5.65 (m, 1H, =CH); 5.02–4.95 (m, 2H, =CH); 3.59–3.50 (m, 1H, CH); 2.61–2.53 (m, 1H, CH); 2.38–2.32 (m, 1H, CH); 1.27 (d, 3H, CH$_3$). |
| 6.50 | 8.90 (s, 1H, pyrimidine); 5.50 (q, 1H, CH); 1.90 (d, 3H, CH$_3$). |
| 6.51 | 8.82 (s, 1H); 4.43 (q, 1H, CH); 2.04 (s, 3H, CH$_3$); 1.67 (d, 3H, CH$_3$). |
| 6.52 | 8.88 (s, 1H, pyrimidine); 8.87 (s, 1H, pyrimidine); 4.76 (q, 1H, CH); 4.63 (q, 1H, CH); 2.61 (s, 3H, CH$_3$); 2.53 (s, 3H, CH$_3$); 1.73 (d, 3H, CH$_3$); 1.68 (d, 3H, CH$_3$). |
| 1.195 | 8.44 (2s, 1H, pyrimidine); 7.85–7.78 (m, 4H); 7.51–7.43 (m, 3H); 5.78–5.68 (m, 2H, NH and =CH); 5.56–5.51 (m, 1H, CH); 5.05–4.94 (m, 2H, =CH); 339–3.33 (m, 1H, CH); 2.55–2.46 (m, 1H, CH); 2.33–2.25 (m, 1H, CH); 1.70 (2d, 3H, CH$_3$); 1.23–1.08 (2d, 3H, CH$_3$). |
| 1.200 | 8.48 (2s, 1H); 7.86–7.80 (m, 4H); 7.51–7.43 (m, 3H); 5.73 (d, 1H, NH); 5.58–5.50 (m, 1H, CH); 4.13 (q, 1H, CH); 2.04 (s, 2H, CH$_3$); 1.70 (2d, 3H, CH$_3$); 1.62–1.55 (2d, 3H, CH$_3$). |
| 1.202 | 8.43 (2a, 1H, pyrimidine); 7.86–7.77 (m, 4H); 7.52–7.44 (m, 3H); 5.84 (d, 1H, NH); 5.57–5.48 (m, 1H, CH); 4.75 (q, 1H, CH); 3.0 (2s, 3H, CH$_3$); 1.81–1.75 (2d, 3H, CH$_3$); 1.70 (2d, 3H, CH$_3$). |

Formulation Examples for active ingredients of formula I (throughout, percentages are by weight)

| 1. Emulsifiable concentrates | a) | b) | c) |
|---|---|---|---|
| a compound of Tables 1 to 5, 7, 8 | 25% | 40% | 50% |

| | | | |
|---|---|---|---|
| calcium dodecylbenzenesulfonate | 5% | 8% | 6% |
| castor oil polyethylene glycol ether (36 mol of ethylene oxide) | 5% | — | — |
| tributylphenol polyethylene glycol ether (30 mol of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| 2. Solutions | a) | b) | c) | d) |
|---|---|---|---|---|
| a compound of Tables 1 to 5, 7, 8 | 80% | 10% | 5% | 95% |
| propylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| petroleum fraction (boiling range 160–190° C.) | — | — | 94% | — |

These solutions are suitable for application in the form of micro-drops.

| 3. Granules | a) | b) | c) | d) |
|---|---|---|---|---|
| a compound of Tables 1 to 5, 7, 8 | 5% | 10% | 8% | 21% |
| kaolin | 94% | — | 79% | 54% |
| highly dispersed silicic acid | 1% | — | 13% | 7% |
| attapulgite | — | 90% | — | 18% |

The active ingredient is dissolved in methylene chloride, the solution is sprayed onto the carrier, and the solvent is evaporated off in vacuo.

| 4. Dusts | a) | b) |
|---|---|---|
| a compound of Tables 1 to 5, 7, 8 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

| 5. Wettable Powders | a) | b) | c) |
|---|---|---|---|
| a compound of Tables 1 to 5, 7, 8 | 25% | 50% | 75% |
| sodium liposulfonate | 5% | 5% | — |
| sodium laurylsulfate | 3% | — | 5% |
| sodium diisobutylnaphthalene sulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 6. Emulsifiable concentrate | |
|---|---|
| a compound of Tables 1 to 5, 7, 8 | 10% |
| octylphenol polyethylene glycol ether (4–5 mol of ethylene oxide) | 3% |
| calcium dodecylbenzenesulfonate | 3% |
| castor oil polyglycol ether (36 mol of ethylene oxide) | 4% |
| cyclohexanone | 30% |
| xylene mixture | 50% |

Emulsions of the required concentration can be obtained from this concentrate by dilution with water.

Biological Examples: A. Microbicidal action

B-1: *Pythium ultimum* on *Beta vulgaris* (sugar beet, "Kleinwanzleben Monogerm") and *Pythium ultimum* on *Zea mays* (maize, "Sweet Corn")

Test method: Mycelium of *Pythium ultimum* is mixed with soil (500 ml of mycelium suspension to 10 liters of soil) and the fungus/soil mixture is introduced into 250 ml plastic trays. After incubation for 4 days at 10° C., 10 seeds of the test plant (maize or sugar beet) are placed in each tray. On the following day, the ways so prepared are each watered with 50 ml of a spray solution (prepared from a 25% wettable powder formulation and water) comprising 0.002% a.i. After a 7-day incubation period at 10° C. and a subsequent 4-day incubation period at 22° C., the action of the test compounds is evaluated on the basis of the number and appearance of the emerged plants. Compounds of Tables 1 to 5, 7 and 8 exhibit good activity against Pythium pathogens.

B-2: Action against *Puccinia graminis* on wheat a) Residual protective action

Wheat plants are sprayed 6 days after sowing with a spray mixture (0.02% active ingredient) prepared from a wettable powder formulation of the test compound. After 24 hours the treated plants are infected with a uredospore suspension of the fungus. The infected plants are incubated for 48 hours at 95–100% relative humidity and about 20° C. and then stood in a greenhouse at about 22° C. Evaluation of rust pustule development is made 12 days after infection.

b) Systemic action

Wheat plants are watered 5 days after sowing with a spray mixture (0.006% active ingredient, based on the volume of the soil) prepared from a wettable powder formulation of the test compound. After 48 hours the treated plants are infected with a uredospore suspension of the fungus. The infected plants are then incubated for 48 hours at 95–100% relative humidity and about 20° C. and then stood in a greenhouse at about 22° C. Evaluation of rust pustule development is made 12 days after infection.

Compounds of Tables 1 to 5, 7 and 8 exhibit good activity against Puccinia fungi. Thus, for example, compounds 1.2 and 2.2 inhibit fungus infestation to 0 to 20%. On the other hand, Puccinia infestation is 100% on untreated and infected control plants.

B-3: Action against *Phytophthora infestans* on tomato plants a) Residual protective action After a cultivation period of 3 weeks, tomato plants are sprayed with a spray mixture (0.02% active ingredient) prepared from a wettable powder formulation of the test compound. After 24 hours the treated plants are infected with a sporangia suspension of the fungus. The infected plants are then incubated for 5 days at 90–100% relative humidity and 20° C. and then evaluated for fungus infestation.

b) Systemic action

After a cultivation period of 3 weeks, a spray mixture (0.006% active ingredient, based on the volume of the soil) prepared from a wettable powder formulation of the test compound is used to water tomato plants. Care is taken that the spray mixture does not come into contact with the parts of the plants above the soil. The treated plants are infected 48 hours later with a sporangia suspension of the fungus. The infected plants are then incubated for 5 days at 90–100% relative humidity and 20° C. and then evaluated for fungus infestation.

Compounds of Tables 1 to 5, 7 and 8 exhibit good protective activity against Phytophthora. Thus, for example, compounds 1.2, 1.18 and 1.19 reduce fungus infestation to 0 to 20%. On the other hand, Phytophthora infestation is 100% on untreated and infected control plants.

B-4: Action against *Cercospora arachidicola* on groundnut plants

Groundnut plants 10–15 cm in height are sprayed with a spray mixture (0.02% active ingredient) prepared from a wettable powder formulation of the test compound, and infected 48 hours later with a conidia suspension of the fungus. The infected plants are incubated for 72 hours at about 21° C. and high humidity and then stood in a greenhouse until the typical leaf specks occur.

Evaluation of the fungicidal action is made 12 days after infection and is based on the number and size of the specks.

Compared with untreated and infected control plants (number and size of the specks=100%), Cercospora infestation on groundnut plants treated with compounds of Tables 1 to 5, 7 and 8 is reduced (10–20%); thus, for example, compounds 1.2, 1.3, 1.53, 1.73, 1.84, 1.86, 1.100 and 1.149.

B-5: Action against *Plasmopara viticola* on vines a) Residual-protective action Vine seedlings in the 4–5 leaf stage are sprayed with a spray mixture (0.02% a.i.) prepared from a wettable powder formulation of the test compound. After 24 hours the treated plants are infected with a sporangia suspension of the fungus. Fungus infestation is evaluated after incubation for 6 days at 95–100% relative humidity and 20° C.

b) Curative action

Vine seedlings in the 4–5 leaf stage are infected with a sporangia suspension of the fungus. After incubation for 24 hours in a humidity chamber at 95–100% relative humidity and 20° C., the infected plants are sprayed with a spray mixture (0.02% active ingredient) prepared from a wettable powder formulation of the test compound. After the spray coating has dried, the treated plants are again placed in the humidity chamber. Evaluation of fungus infestation is made 6 days after infection.

Compounds of Tables 1 to 5, 7 and 8 exhibit good protective activity against *Plasmopara viticola* (less than 20% infestation); thus, for example, compounds 1.2 and 1.18. On the other hand, Plasmopara infestation is 100% on untreated and infected control plants.

B-6: Action against *Pyricularia oryzae* on rice plants a) Residual protective action After a cultivation period of 2 weeks, rice plants are sprayed with a spray mixture (0.02% active ingredient) prepared from a wettable powder formulation of the test compound. After 48 hours the treated plants are infected with a conidia suspension of the fungus. Evaluation of fungus infestation is made after incubation for 5 days at 95–100% relative humidity and about 22° C.

b) Systemic action 2-week-old rice plants are watered with a spray mixture (0.006% active ingredient, based on the volume of the soil) prepared from a wettable powder formulation of the test compound. The pots are then filled with water so that the lowermost parts of the stems of the rice plants stand in water. After 96 hours, the treated plants are infected with a conidia suspension of the fungus. The infected rice plants are then stood in a greenhouse at about 22° C. and evaluation of fungus infestation is made after 10 days. The infected plants are then incubated for 5 days at 95–100% relative humidity and about 24° C. and then evaluated for fungus infestation.

Compared with untreated control plants (infestation= 100%), rice plants treated with a spray mixture based on the compounds of Tables 1 to 5 exhibit only slight fungus infestation. Thus, for example, compounds nos. 1.2, 1.3, 1.53, 1.73, 1.84, 1.86, 1.100 and 1.149 in test (a) and compounds nos. 1.46 and 1.47 in test (b) reduce fungus infestation to 0to 10%.

B-7: Residual-protective action against *Venturia inaequalis* on apple shoots

Apple cuttings with 10–20 cm long fresh shoots are sprayed with a spray mixture (0.02% a.i.) prepared from a wettable powder formulation of the test compound. The treated plants are infected 24 hours later with a conidia suspension of the fungus. The plants are then incubated for 5 days at 90–100% relative humidity and stood in a greenhouse for a further 10 days at 20°–24° C. Scab infestation is evaluated 15 days after infection.

Compounds of Tables 1 to 5 exhibit good protective activity against Venturia.

B-8: Action against *Erysiphae graminis* on barley a) Residual-protective action Barley plants about 8 cm in height are sprayed with a spray mixture (0.02% active ingredient) prepared from a wettable powder formulation of the test compound. The treated plants are dusted with conidia of the fungus after 3 to 4 hours. The infected barley plants are stood in a greenhouse at about 22° C. The fungus infestation is evaluated after 10 days.

b) Systemic action

A spray mixture (0.002% active ingredient, based on the volume of the soil) prepared from a wettable powder formulation of the test compound is used to water barley plants about 8 cm in height. Care is taken that the spray mixture does not come into contact with the parts of the plants above the soil. The treated plants are dusted 48 hours later with conidia of the fungus. The infected barley plants are then stood in a greenhouse at about 22° C. and evaluation of fungus infestation is made after 10 days.

Compounds of the formulae of Tables 1 to 5, 7 and 8 exhibit good activity against Erysiphae fungi. Erysiphae infestation is 100% on untreated and infected control plants. Of the compounds of the Tables, compounds nos. 1.2, 1.3, 1.53, 1.73, 1.84, 1.86, 1.100 and 1.149 inhibit fungus infestation to 0 to 5%.

Biological Examples: B. Acaricidal/insecticidal action

B-9: Action against *Tetranychus urticae*

Young bean plants are populated with a mixed population of *Tetranychus urticae* and sprayed one day later with an aqueous emulsion comprising 400 ppm of the test compound. The plants are then incubated for 6 days at 25° C. and then evaluated. The percentage reduction in the population (% activity) is determined by comparing the number of dead eggs, larvae and adults on the treated plants with that on untreated plants.

Compounds of Table 1 exhibit good activity against *Tetranychus urticae* in this test. In particular, compounds 1.2, 1.3, 1.9, 1.43, 1.53, 1.55, 1.58, 1.84, 1.149, 3.1 and 3.3 are more than 80% effective.

B-10: Action against *Nilaparvata lugens*

Rice plants are sprayed with an aqueous emulsion comprising 400 ppm of test compound. After the spray coating has dried, the rice plants are populated with cicada larvae in the 2nd and 3rd stages. Evaluation is made 21 days later. The percentage reduction in the population (% activity) is determined by comparing the number of surviving cicadas on the treated plants with that on untreated plants.

Compounds of Table 1 exhibit good activity against *Nilaparvata lugens* in this test. In particular, compounds 1.2, 1.3 and 1.9 are more than 80% effective.

B-11: Action against *Nephotettix cincticeps*

Rice plants are sprayed with an aqueous emulsion comprising 400 ppm of test compound. After the spray coating has dried, the rice plants are populated with cicada larvae in the 2nd and 3rd stages. Evaluation is made 21 days later. The percentage reduction in the population (% activity) is determined by comparing the number of surviving cicadas on the treated plants with that on untreated plants.

Compounds of Table 1 exhibit good activity against *Nephotettix cincticeps* in this test. In particular, compound 1.2 is more than 80% effective.

B-12: Action against *Bemisia tabaci*

Dwarf bean plants are placed in gauze cages and populated with adults of *Bemisia tabaci* (whitefly). When oviposition has taken place, all the adults are removed and 10 days later the plants and the nymphs located thereon are sprayed with an aqueous emulsion of the test compounds (concentration 400 ppm). Evaluation is made 14 days after application of the test compound by determining the % hatching rate in comparison with untreated controls.

In this test, compounds of Table 1 exhibit good activity against *Bemisia tabaci*. In particular, compound no. 1.2 is more than 80% effective.

B-13: Ovicidal/larvicidal action against *Heliothis virescens*

Egg deposits of *Heliothis virescens* on cotton are sprayed with an aqueous emulsion comprising 400 ppm of the test compound. 8 days later, the percentage of eggs which have hatched and the survival rate of the caterpillars are evaluated in comparison with untreated controls (% reduction in the population).

In this test, compounds of Table 1 exhibit good activity against *Heliothis virescens*. In particular, compounds 1.2, 1.3 and 1.9 are more than 80% effective.

B-14: Action against a mixed population of *Tetranychus cinnabarinus*

Dilution series

DWARF BEANS in the 2-leaf stage are populated with a mixed population (eggs, larvae/nymphs, adults) of an OP-tolerant strain of *TETRANYCHUS CINNABARINUS*. The test compounds are applied to the plants 24 hours after infection in metered mounts of 200, 100, 50 mg a.i./l in an automatic spraying chamber. The test compounds are formulated and are diluted to the corresponding amounts with water. The test is evaluated 2 and 7 days after application for % mortality against eggs, larvae/nymphs, adults.

Compounds of Tables 1 to 5 exhibit over 80% mortality in dilutions down to 50 mg a.i./liter. The respective (–)-enantiomers are also effective in even smaller amounts.

What is claimed is:

1. A compound of formula I

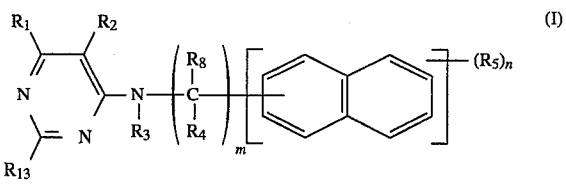

wherein:

$R_1$ is hydrogen; $C_1$–$C_5$alkyl; $C_1$–$C_5$haloalkyl having from 1 to 3 halogen atoms; $C_2$–$C_5$alkoxyalkyl; $C_2$–$C_5$alkenyl; $C_2$–$C_5$haloalkenyl; or halogen;

$R_2$ is hydrogen; $C_1$–$C_5$alkyl; $C_1$–$C_3$haloalkyl having from 1 to 3 halogen atoms; $C_3$–$C_5$alkoxyalkyl; nitro; cyano; $S(O)_p$-$C_1$–$C_4$alkyl or halogen;

$R_3$ is hydrogen; $C_1$–$C_3$alkyl; benzyl; —CO—$R_6$; or $SR_7$;

$R_4$ and $R_8$ are each independently of the other hydrogen; $C_1$–$C_5$alkyl; $C_1$–$C_5$haloalkyl having from 1 to 3 halogen atoms; $C_2$–$C_6$alkoxyalkyl; or $C_3$–$C_6$cycloalkyl;

$R_5$ is halogen; $C_1$–$C_3$alkyl; $C_1$–$C_3$alkoxy; $C_1$–$C_6$alkoxyalkyl; $C_1$–$C_3$haloalkyl; $C_1$–$C_3$alkylthio; $C_1$–$C_3$haloalkoxy; $C_1$–$C_3$haloalkylthio; cyano; or nitro;

$R_6$ is $C_1$–$C_5$alkyl; phenyl; or phenyl substituted by halogen and/or by $C_1$–$C_3$alkyl;

$R_7$ is phenyl; phenyl mono- or di-substituted by halogen, nitro or by cyano; benzyl; benzyl mono- or di-substituted in the ring by halogen, nitro or by cyano; $C_1$–$C_5$alkyl; or $C_1$–$C_5$alkyl substituted by halogen or by cyano;

$R_9$ is $C_1$–$C_5$alkyl;

$R_{10}$ is hydrogen or $C_1$–$C_3$alkyl;

$R_{13}$ is hydrogen or $C_1$–$C_4$alkyl;

m is 1, 2 or 3;

n is 0, 1 or 2; and p is 0, 1 or 2.

2. A compound of formula I''' according to claim 1

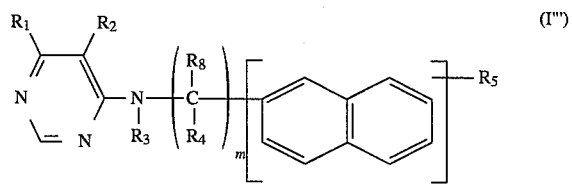

wherein $R_1$ is hydrogen, $C_1$–$C_3$alkyl, $CF_3$ or halogen;

$R_2$ is hydrogen, $C_1$–$C_3$alkyl, halogen, $NO_2$ or $S(O)_p$-$C_1$–$C_3$alkyl;

$R_3$ is hydrogen;

$R_4$ is methyl, ethyl, isopropyl, n-propyl or cyclopropyl;

$R_8$ is hydrogen, methyl or ethyl;

$R_5$ is hydrogen, halogen, $C_1$–$C_3$alkyl, $OCHF_2$, $CF_3$, $NO_2$ or $C_1$–$C_3$alkoxy;

m is 1 or 2; and p is 0, 1 or 2.

3. A compound of formula Ia according to claim 1

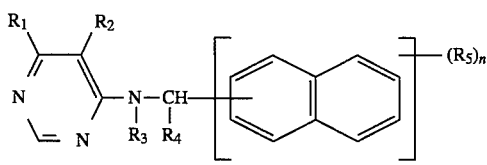

(Ia)

wherein:

$R_1$ is $C_1$–$C_5$alkyl that is unsubstituted or substituted by 1–3 halogen or by $C_1$–$C_3$alkoxy; $C_2$–$C_5$alkenyl that is unsubstituted or substituted by halogen; or halogen;

$R_2$ is $C_1$–$C_5$alkyl that is unsubstituted or substituted by 1–3 halogen or by $C_1$–$C_3$alkoxy; halogen; nitro; or cyano;

$R_3$ is hydrogen; $C_1$–$C_5$alkyl; benzyl; —CO—$R_6$ or —S—$R_7$;

$R_4$ is hydrogen; $C_1$–$C_5$alkyl that is unsubstituted or substituted by 1–3 halogen or by $C_1$–$C_3$alkoxy; or $C_3$–$C_6$cycloalkyl;

$R_5$ is halogen; $C_1$–$C_3$alkyl; $C_1$–$C_3$alkoxy; or $C_1$–$C_3$alkylthio;

$R_6$ is $C_1$–$C_5$alkyl; or phenyl that is unsubstituted or substituted by halogen and/or by $C_1$–$C_3$alkyl;

$R_7$ is phenyl or benzyl each of which is unsubstituted or mono- or di-substituted in the ring by identical or different substituents selected from halogen, nitro and cyano; or $C_1$–$C_5$alkyl that is unsubstituted or substituted by halogen or by cyano; and n is 0, 1, 2 or 3.

4. A compound according to claim 1 wherein $R_1$ is $C_1$–$C_5$alkyl; $CF_3$; $C_2$–$C_5$alkoxyalkyl; $C_2$–$C_4$alkenyl; $C_2$–$C_4$monohaloalkenyl; or halogen;

$R_2$ is $C_1$–$C_5$alkyl or halogen;

$R_3$ is hydrogen or $C_1$–$C_3$alkyl $R_4$ is hydrogen; $C_1$–$C_3$alkyl; or cyclopropyl;

$R_5$ is halogen; $C_1$–$C_2$alkyl; or $C_1$–$C_3$alkoxy;

$R_8$ is hydrogen;

n is 0, 1 or 2; and m is 1.

5. A compound according to claim 4, wherein $R_1$ is $C_1$–$C_4$alkyl; $CF_3$; $C_2$–$C_4$alkoxyalkyl; $C_2$–$C_4$ alkenyl; or halogen;

$R_4$ is hydrogen or $C_1$–$C_3$alkyl; and $R_5$ is halogen; methyl; ethyl; or methoxy.

6. A compound according to claim 3, wherein n is 0.

7. A compound according to claim 5, wherein $R_1$ is $C_2H_5$;

$R_2$ Cl;

$R_3$ is H;

$R_4$ is $CH_3$;

$R_{13}$ hydrogen; and n is 0.

8. A compound of formula I according to claim 1 from the group:

(d,l)-4-[1'-(β-naphthyl)-ethylamino]-5-chloro-6-ethylpyrimidine;

(−)-4-[1'-(β-naphthyl)-ethylamino]-5-chloro-6-ethylpyrimidine;

(d,l)-4-[1'-(β-naphthyl)-propylamino]-5-chloro-6-ethylpyrimidine;

(d,l)-4-[1'-(β-naphthyl)-ethylamino]-5-chloro-6-methylpyrimidine;

(d,l)-4-[1'-(2-(6-bromonaphthyl))-ethylamino]-5-chloro-6-ethylpyrimidine;

(d,l)-4-[1'-(β-naphthyl)-ethylamino]-5-bromo-6-ethylpyrimidine;

(d,l)-4-[1'-(β-naphthyl)-ethylamino]-5-chloro-6-n-propylpyrimidine;

(d,l)-4-[1'-(β-naphthyl)-ethylamino]-5-iodo-6-ethylpyrimidine.

9. The compound (−)-4-[1'-(β-naphthyl)-ethylamino]-5-chloro-6-ethylpyrimidine according to claim 7.

10. A method of protecting plants against attack by phytopathogenic microorganisms, which comprises applying a fungicidally effective amount of a compound according to claim 1 as active ingredient to the plants or to the locus thereof.

11. A method according to claim 10 wherein the phytopathogenic microorganisms are fungus organisms.

12. A method of protecting plants against attack by phytopathogenic microorganisms, which comprises applying a fungicidally effective amount of a compound according to claim 4 as active ingredient to the plants or to the locus thereof.

13. A method of protecting plants against attack by phytopathogenic microorganisms, which comprises applying a fungicidally effective amount of a compound according to claim 5 as active ingredient to the plants or to the locus thereof.

14. A method of protecting plants against attack by phytopathogenic microorganisms, which comprises applying a fungicidally effective amount of a compound according to claim 6 as active ingredient to the plants or to the locus thereof.

* * * * *